United States Patent
Dumas et al.

(10) Patent No.: US 7,329,670 B1
(45) Date of Patent: Feb. 12, 2008

(54) INHIBITION OF RAF KINASE USING ARYL AND HETEROARYL SUBSTITUTED HETEROCYCLIC UREAS

(75) Inventors: Jacques Dumas, Orange, CT (US); Uday Khire, Hamden, CT (US); Timothy B. Lowinger, Nishinomiya (JP); Bernard Riedl, Branford, CT (US); William J. Scott, Guilford, CT (US); Roger A. Smith, Madison, CT (US); Jill E. Wood, Hamden, CT (US); Holia Hatoum-Mokdad, Hamden, CT (US); Jeffrey Johnson, Branford, CT (US); Aniko Redman, Derby, CT (US); Robert Sibley, North Haven, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 09/472,232

(22) Filed: Dec. 27, 1999

Related U.S. Application Data

(63) Continuation of application No. 09/303,621, filed on Dec. 22, 1998, now abandoned.

(60) Provisional application No. 60/135,502, filed on Dec. 22, 1997.

(51) Int. Cl.
*C07D 231/38* (2006.01)
*C07D 403/12* (2006.01)
*A61K 31/415* (2006.01)

(52) U.S. Cl. .................... 514/275; 514/333; 514/341; 514/407; 544/333; 546/256; 546/275.4; 548/371.7

(58) Field of Classification Search ............. 548/371.7; 544/333; 546/256, 275.4; 514/275, 333, 514/341, 407
See application file for complete search history.

(56) References Cited

U.S. PATENT DOCUMENTS

| | | | |
|---|---|---|---|
| 2,046,375 A | 7/1936 | Goldstein et al. ........... 260/125 |
| 2,093,265 A | 9/1937 | Coffby et al. .............. 260/125 |
| 2,288,422 A | 6/1942 | Rohm ...................... 260/506 |
| 2,649,476 A | 8/1953 | Martin |
| 2,683,082 A | 7/1954 | Hill et al. ................... 44/71 |
| 2,722,544 A | 11/1955 | Martin |
| 2,745,874 A | 5/1956 | Schetty et al. .............. 260/553 |
| 2,781,330 A | 2/1957 | Downey .................... 260/45.9 |
| 2,797,214 A | 6/1957 | Bossard |
| 2,867,659 A | 1/1959 | Model et al. ............... 260/552 |
| 2,877,268 A | 3/1959 | Applegate et al. ........... 260/553 |
| 2,960,488 A | 11/1960 | Tamblyn et al. ............. 260/45.9 |
| 2,973,386 A | 2/1961 | Weldon .................... 260/553 |
| 3,151,023 A | 9/1964 | Martin ...................... 167/30 |
| 3,200,035 A | 8/1965 | Martin et al. ............... 167/38.6 |
| 3,230,141 A | 1/1966 | Frick et al. ................ 167/38.6 |
| 3,424,760 A | 1/1969 | Helsley et al. .............. 260/326.3 |
| 3,424,761 A | 1/1969 | Helsley et al. ............. 260/326.3 |
| 3,424,762 A | 1/1969 | Helsley et al. ............. 260/326.3 |
| 3,547,940 A | 12/1970 | Brantley .................... 260/307 |
| 3,646,059 A | 2/1972 | Brantley .................... 260/310 |
| 3,689,550 A | 9/1972 | Schellenbaum et al. ...... 260/553 |
| 3,743,498 A | 7/1973 | Brantley ..................... 71/88 |
| 3,754,887 A | 8/1973 | Brantley ..................... 71/74 |
| 3,823,161 A | 7/1974 | Lesser ..................... 260/332.2 |
| 3,828,001 A | 8/1974 | Broad et al. ............... 260/332.2 |
| 3,860,645 A | 1/1975 | Nikawitz ................... 260/553 |
| 3,990,879 A | 11/1976 | Soper ........................ 71/66 |
| 4,001,256 A | 1/1977 | Callahan et al. ........ 260/295 E |
| 4,009,847 A | 3/1977 | Aldrich et al. ............ 424/275 |
| 4,042,372 A | 8/1977 | Harper ....................... 71/90 |
| 4,062,861 A | 12/1977 | Yukinaga et al. ........ 260/307 H |
| 4,071,524 A | 1/1978 | Banitt ................... 260/293.77 |
| 4,111,680 A | 9/1978 | Yukinaga et al. ............ 71/104 |
| 4,111,683 A | 9/1978 | Singer ...................... 71/104 |
| 4,116,671 A | 9/1978 | Yukinaga et al. ............. 71/88 |
| 4,173,637 A | 11/1979 | Nishiyama et al. .......... 424/263 |
| 4,173,638 A | 11/1979 | Nishiyama et al. .......... 424/263 |
| 4,183,854 A | 1/1980 | Crossley .................... 548/195 |
| 4,212,981 A | 7/1980 | Yukinaga et al. ........... 548/246 |
| 4,240,820 A | 12/1980 | Dickore et al. .............. 71/76 |
| 4,279,639 A | 7/1981 | Okamoto et al. |
| 4,405,644 A | 9/1983 | Kabbe et al. ............... 424/322 |
| 4,410,697 A | 10/1983 | Török et al. ................ 544/165 |
| 4,437,878 A | 3/1984 | Acker et al. ................. 71/90 |
| 4,468,380 A | 8/1984 | O'Doherty et al. ......... 424/114 |

(Continued)

FOREIGN PATENT DOCUMENTS

CA 2146707 10/1995

(Continued)

OTHER PUBLICATIONS

Simone, Oncology: Introduction, Cecil Textbook of Medicine, 20th Edition, vol. 1, pp. 1004-1010, 1996.*

(Continued)

*Primary Examiner*—Deepak Rao
(74) *Attorney, Agent, or Firm*—Millen, White, Zelano & Branigan, P.C.

(57) ABSTRACT

The compounds are aryl and heteroaryl substituted heterocyclic ureas of the formula A—NH—C(O)—NH—B where A is the aryl or hetaryl substituted heterocyclic group and B is an aryl or heteroaryl moiety. The compounds inhibit raf kinase and are useful in the treatment of RAF kinase mediated diseases.

7 Claims, No Drawings

U.S. PATENT DOCUMENTS

| | | | |
|---|---|---|---|
| 4,473,579 A | 9/1984 | Devries et al. | 424/282 |
| 4,511,571 A | 4/1985 | Böger et al. | 514/351 |
| 4,514,571 A | 4/1985 | Nakai et al. | 546/306 |
| 4,526,997 A | 7/1985 | O'Doherty et al. | 560/21 |
| 4,623,662 A | 11/1986 | De Vries | 514/596 |
| 4,643,849 A | 2/1987 | Hirai et al. | 540/597 |
| 4,740,520 A | 4/1988 | Hallenbach et al. | 514/447 |
| 4,760,063 A | 7/1988 | Hallenbach et al. | 514/230.5 |
| 4,808,588 A | 2/1989 | King | 514/212 |
| 4,820,871 A | 4/1989 | Kissener et al. | 564/55 |
| 4,863,924 A | 9/1989 | Haga et al. | 514/247 |
| 4,973,675 A | 11/1990 | Israel et al. | |
| 4,983,605 A | 1/1991 | Kondo et al. | 514/247 |
| 4,985,449 A | 1/1991 | Haga et al. | 514/349 |
| 5,036,072 A | 7/1991 | Nakajima et al. | 514/274 |
| 5,059,614 A | 10/1991 | Lepage et al. | 514/378 |
| 5,098,907 A | 3/1992 | Kondo et al. | 514/274 |
| 5,130,331 A | 7/1992 | Pascual | 514/447 |
| 5,162,360 A | 11/1992 | Creswell et al. | 514/371 |
| 5,185,358 A | 2/1993 | Creswell | 514/383 |
| 5,312,820 A | 5/1994 | Ashton et al. | 514/227.5 |
| 5,319,099 A | 6/1994 | Kamata et al. | 548/538 |
| 5,399,566 A | 3/1995 | Katano et al. | 514/340 |
| 5,423,905 A | 6/1995 | Fringeli | 106/18.32 |
| 5,429,918 A | 7/1995 | Seto et al. | 430/551 |
| 5,447,957 A | 9/1995 | Adams et al. | |
| 5,470,882 A | 11/1995 | Dixon et al. | 514/596 |
| 5,500,424 A | 3/1996 | Nagamine et al. | 514/235.5 |
| 5,508,288 A | 4/1996 | Forbes et al. | 514/310 |
| 5,596,001 A | 1/1997 | Hamanaka | |
| 5,597,719 A | 1/1997 | Freed et al. | 435/194 |
| 5,696,138 A | 12/1997 | Olesen et al. | 514/349 |
| 5,698,581 A | 12/1997 | Kleemann et al. | 514/447 |
| 5,773,459 A | 6/1998 | Tang et al. | 514/585 |
| 5,780,483 A | 7/1998 | Widdowson et al. | 514/311 |
| 5,807,891 A | 9/1998 | Bold et al. | 514/487 |
| 5,814,646 A | 9/1998 | Heinz | 514/363 |
| 5,886,044 A | 3/1999 | Widdowson et al. | |
| 5,891,895 A | 4/1999 | Shiraishi et al. | |
| 5,908,865 A | 6/1999 | Doi et al. | 514/635 |
| 5,929,250 A | 7/1999 | Widdowson et al. | |
| 5,965,573 A | 10/1999 | Petrie et al. | |
| 6,004,965 A | 12/1999 | Breu et al. | |
| 6,005,008 A | 12/1999 | Widdowson et al. | |
| 6,015,908 A | 1/2000 | Widdowson et al. | |
| 6,020,345 A | 2/2000 | Vacher et al. | |
| 6,022,884 A | 2/2000 | Mantlo et al. | |
| 6,043,374 A | 3/2000 | Widdowson et al. | |
| 6,080,763 A * | 6/2000 | Regan et al. | 514/341 |
| 6,093,742 A | 7/2000 | Salituro et al. | 514/596 |
| 6,133,319 A | 10/2000 | Widdowson | |
| 6,143,764 A | 11/2000 | Kubo et al. | |
| 6,147,116 A | 11/2000 | Barbachyn et al. | |
| 6,174,901 B1 | 1/2001 | Mantlo et al. | |
| 6,180,675 B1 | 1/2001 | Widdowson et al. | |
| 6,211,373 B1 | 4/2001 | Widdowson et al. | |
| 6,218,539 B1 | 4/2001 | Widdowson | |
| 6,242,601 B1 | 6/2001 | Breu et al. | |
| 6,262,113 B1 | 7/2001 | Widdowson et al. | |
| 6,271,261 B1 | 8/2001 | Widdowson | |
| 6,319,921 B1 * | 11/2001 | Cirillo et al. | 514/236.5 |
| 6,333,341 B1 | 12/2001 | Mantlo et al. | |
| 6,339,045 B1 | 1/2002 | Kanno et al. | |
| 6,344,476 B1 | 2/2002 | Ranges et al. | |
| 6,391,917 B1 | 5/2002 | Petrie et al. | |
| 2002/0062763 A1 | 5/2002 | Macholdt et al. | |
| 2002/0065296 A1 | 5/2002 | Dumas et al. | |
| 2002/0082255 A1 | 6/2002 | Eastwood | |
| 2002/0128321 A1 | 9/2002 | Widdowson et al. | |

FOREIGN PATENT DOCUMENTS

| | | |
|---|---|---|
| DE | 0 487 014 | 12/1929 |
| DE | 0 511 468 | 10/1930 |
| DE | 0 523 437 | 5/1931 |
| DE | 2436179 | 2/1975 |
| DE | 25 01 648 | 7/1975 |
| DE | 3305866 A1 | 2/1983 |
| DE | 35 29 247 A1 | 8/1985 |
| DE | 35 40 377 A1 | 11/1985 |
| DE | 0 253 997 | 2/1988 |
| DE | 3540377 A1 | 7/1988 |
| EP | 16371 | 3/1980 |
| EP | 0107214 A1 | 5/1984 |
| EP | 0116932 A1 | 8/1984 |
| EP | 0192263 B1 | 8/1986 |
| EP | 0230400 A2 | 7/1987 |
| EP | 0233559 B1 | 8/1987 |
| EP | 242666 | 10/1987 |
| EP | 0264904 A2 | 4/1988 |
| EP | 335156 | 3/1989 |
| EP | 371876 | 11/1989 |
| EP | 0359148 A1 | 3/1990 |
| EP | 0379915 A1 | 8/1990 |
| EP | 0380048 A2 | 8/1990 |
| EP | 0381987 A1 | 8/1990 |
| EP | 425443 | 10/1990 |
| EP | 0 405 233 | 1/1991 |
| EP | 04085233 A1 | 1/1991 |
| EP | 459887 | 5/1991 |
| EP | 0 502 504 | 9/1992 |
| EP | 676395 | 7/1996 |
| EP | 860433 | 8/1998 |
| EP | 0860433 A1 | 8/1998 |
| FR | 1 457 172 | 9/1966 |
| GB | 0 828 231 | 10/1956 |
| GB | 0 771 333 | 3/1957 |
| GB | 0 921 682 | 3/1963 |
| GB | 1590870 | 6/1981 |
| IR | 26555 | 1/2000 |
| JP | 44 2569 | 2/1969 |
| JP | 50-76072 | 6/1975 |
| JP | 50-149668 | 11/1975 |
| JP | 51 063170 | 6/1976 |
| JP | 51-80862 | 7/1976 |
| JP | 53 086033 | 7/1978 |
| JP | 54-032468 | 9/1979 |
| JP | 55 98152 | 7/1980 |
| JP | 50-77375 | 9/1980 |
| JP | 55-124763 | 9/1980 |
| JP | 55-162772 | 12/1980 |
| JP | 3 532 47 | 3/1991 |
| JP | 8 301841 | 11/1996 |
| JP | 10-306078 | 11/1998 |
| LB | 6124 | 1/2000 |
| WO | 96/02112 | 3/1990 |
| WO | 93/18028 | 9/1993 |
| WO | 93/24458 | 12/1993 |
| WO | 94/14801 | 7/1994 |
| WO | 94/18170 | 8/1994 |
| WO | 94 22807 | 10/1994 |
| WO | 94/25012 | 11/1994 |
| WO | 95/02591 | 1/1995 |
| WO | 95/07922 | 3/1995 |
| WO | 95/13067 | 5/1995 |
| WO | 95/31451 | 11/1995 |
| WO | 95/33458 | 12/1995 |
| WO | WO 96/10559 | 4/1996 |
| WO | WO 96/13632 | 5/1996 |
| WO | 96/25157 A1 | 8/1996 |
| WO | 96/40673 | 12/1996 |

| | | |
|---|---|---|
| WO | A1 96/40675 | 12/1996 |
| WO | 97/29743 | 8/1997 |
| WO | 97/30992 | 8/1997 |
| WO | 97/40028 A1 | 10/1997 |
| WO | 97/45400 | 12/1997 |
| WO | 97/49399 | 12/1997 |
| WO | 97/49400 | 12/1997 |
| WO | WO 98/17267 | 4/1998 |
| WO | 98/22103 | 5/1998 |
| WO | 98/22432 | 5/1998 |
| WO | 97/17329 | 8/1998 |
| WO | 98/52559 | 11/1998 |
| WO | WO 98/52558 | 11/1998 |
| WO | WO 98/52559 | 11/1998 |
| WO | WO 99/33458 | 11/1998 |
| WO | 99/00357 | 1/1999 |
| WO | 99/00370 | 1/1999 |
| WO | WO 99/20617 | 4/1999 |
| WO | WO 99/32110 | 4/1999 |
| WO | 99/23091 | 5/1999 |
| WO | 99/24398 | 5/1999 |
| WO | WO 99/21835 | 5/1999 |
| WO | WO 99/24635 | 5/1999 |
| WO | 99/32111 | 7/1999 |
| WO | 99/32437 | 7/1999 |
| WO | 99/32455 | 7/1999 |
| WO | WO 99/32106 | 7/1999 |
| WO | WO 99/32436 | 7/1999 |
| WO | WO 99/32463 | 7/1999 |
| WO | 00/17175 | 9/1999 |
| WO | 00/43384 | 7/2000 |
| WO | WO 00/41698 | 7/2000 |
| WO | WO 00/42012 | 7/2000 |
| WO | WO 00/43366 | 7/2000 |
| WO | WO 0047577 | 8/2000 |
| WO | 00/55139 | 9/2000 |
| WO | 00/55152 | 9/2000 |
| WO | WO 01/36403 A1 | 5/2001 |
| WO | WO 02/24635 A2 | 3/2002 |

OTHER PUBLICATIONS

Bruder et al., Adenovirus Infection Stimulates the Raf/MAPK Signaling Pathway and Induces Interleukin-8 Expression, Journal of Virology, vol. 71, No. 1, pp. 398-404, Jan. 1997.*
Abstract of EP 116,932, Aug. 1984.
Abstract of EP 676,395, Oct. 1995.
Abstract of EP 202,538, Nov. 1986.
Abstract of EP 16,371, Oct. 1980.
Avruch et al., "Raf meets Ras: completing the framework of a signal transduction pathway", TIBS 19; Jul. 1994; pp. 279-281.
White, A.D., et al., "Heterocyclic Ureas: Inhibitors of Acyl-CoA:Cholesterol O-Acyltransferase as Hypochelesterolemic Agents," J. Med. Chem , 39(22) Jun. 6, 1996, pp. 4382-4395.
Audia, James E., et al., "Potent Selective Tetraphydro-β-carboline Antagonists of the Serotonin 2B (5HT$_{2B}$) Contractile Receptor in the Rat Stomach Fundus," J. Med. Chem., 39(14) Jan. 22, 1996, pp. 2773-2780.
Forbes, Ian T., "N-(1-Methyl-5-indolyl)-N-(3-methyl-5-isothiazolyl)urea: A Novel, High-Affinity 5-HT$_{2B}$ Receptor Antagonist," J. Med. Chem., 38(6) Mar. 17, 1995, pp. 855-857.
Boulton, A. J., et al., "Heterocyclic Rearrangements. Part X.[1] A Generalised Monocyclic Rearrangement," J. Chem. Soc. (C) 1967, 2005-07.
N. S. Magnuson, et al., "The Raf-1 serine/threonine protein kinase," Cancer Biology, vol. 5, 1994, pp. 247-253.
G. Daum, et al., The ins and outs of Raf Kinases,: TIBS 19, Nov. 1994, pp. 474-480.
W. Kolch, et al., "Raf-1 protein kinase is required for growth of induced NIH/373 cells," Letters to Nature, vol. 349, Jan. 31, 1991, pp. 226-228.

M. Fridman, et al., "The Minimal Fragments of c-Raf-1 and NF1 That Can Suppress v-Ha-Ras-Induced Malignant Phenotype," The Journal of Biological Chemistry, vol. 269, No. 48, Dec. 2, 1994, pp. 30105-30108.
G. L. Bolton, et al., Chapter 17. Ras Oncogene Directed Approaches in Cancer Chemotherapy, Annual Reports In Medicinal Chemistry, vol. 29, 1994, pp. 165-174.
J. L. Bos, "ras Oncogenes in Human Cancer: A Review," Cancer Research, vol. 49, Sep. 1, 1989, pp. 4682-4689.
Michaelis, Justus, Liebigs Ann. Chem. (JLACBF) 397, 1913, 143.
B. P. Monia, et al., "Antitumor activity of a phosphorothioate antisense oligodeopxynucleotide targeted against C-raf kinase," Nature Medicine, vol. 2, No. 6, Jun. 1996, pp. 668-675.
Lee, et al., Bicyclic Imidazoles as a Novel Class of Cytokine Biosynthesis Inhiibitors, N.Y. Academy of Science, 1993, pp. 149-170.
F. Lepage, et al., "New N-aryl isoxazolecarboxamides and N-isoxazolybenzamides as anticonvulsant agents," Eur. J. Med. Chem, vol. 27, 1992, pp. 581-593.
Ridley, et al., "Actions of IL-1 are Selectively Controlled by p38 Mitogen-Activated Protein Kinase," The American Association of Immunologists, 1997, p. 3165-3173.
Chemical Abstract, vol. 116, No. 21, May 25, 1992, pp. 741-742.
Tarzia, G. et al. Whythesis and antiinflammatory properties of some pyrrol(1H,3H)[3,4] pyrimidin-2-onesandpyrrolo(1H,3H)[3,4-d] pyurimidin-2-ones and pyrrolo(1H,3H)-pyrimidin-2-ones. Chemical Abstracts. Aug. 27, 1979, No. 74558; p. 594.
Kubo, Hiroshi et al: "herbicidal activity . . . " J. Agr. Food Chem, (1970), 18(1), 60-5.
Russo, F. et al. "Synthesis of 2,6-substituted derivatives of 5H-1,3,4-thiadiazolo'3,2-al-s triazine-5,7-dione" Farmaco, Ed.Sci. (1978), 33(12), 972-83.
Foussard-Blanpin, Odette: "Comparative pharmacodynamic study of variously substituted carboxamides of the central nervous ststem" Ann. Pharm. Fr. (1982), 40 (4), 339-50.
Grant, A.M et al.: "Hypotensive thiadiazoles" J. Med. Chem. (1972), 15(10), 1082-4.
Abstract of EP 676,695 (U.S. equivalent 5,698,581), 1997.
Abstract of EP 4931 (U.S. equivalent 4,240,820), 1980.
Abstract of De 3305866 (EP equivalent 116,932), 1994.
Abstract of EP 202,538, 1985.
Murata et al. Chemical and Pharmaceutical Bulletin, vol. 22, 1974 pp. 1212-1213.
Garcia-Lopez et al. Journal of the American Chemical Society , vol. 1978, 1978, pp. 438-7.
English abstract EP425443, 1990.
English Abstract WO9932437, 1999.
Caplus 95:61995, Abstract JP 55162772, Substituted acetic derivatives, Shionogi & Co., May 23, 1980.
Caplus 86:72448, Abstract JP 57053785, Pyridine derivatives, Maeda Ryozo et al., Nov. 15, 1982.
Caplus 84:180049, Abstract JP 56029871, Hamada Yoshinori et al., Jul. 10, 1981.
Caplus 84:43857, Abstract JP 58021626, Maeda Ryozo et al., May 2, 1983.
Caplus 113:106314, Abstract of JP 2022650, Silver halide color photographic material containing a cyan coupter of 2-ureido-phenol type to improve dye developability and remove lecuo cyan dye, Noboru Mizukura et al. Jan. 25, 1990.
Caplus 113:142130, Abstract of JP 2023337, Silver halide photographic material containing phenolic cyan coupler a colorless cyan coupler, Toshihiko Yagi et al., Jan. 25, 1990.
Caplus 87:62295, "The metabolism and toxicity of halogenated carbanilides. Biliary metabolites of 3,4,4'-trichlorocarbanilide and 3-trifluoromethyl-4,4'-dichlorocarbanilide in the rat", Chemical Life Science, pp. 157-166, 1977.
Caplus 127:293717, "Optical properties of segmented oligourethane with azomethine terminal fragments", National Academy of Science of Ukraine, M. V. Kurik et al., pp. 2038-2041, 1996.
Caplus 127:273945, "Quantitative structure-biodegradability studies: an investigation of the MITI aromatic compound database", School of Pharmacy and Chemistry, J. C. Dearden, pp. 93-104, 1996.

Caplus 126:166148, "Inhibitors of coenzyme A-independent transacylase induce apoptisis in human HL-60 cells", James D. Winkler et al., J. Pharmacol. Exp. Ther. pp. 956-966, 1996.

Caplus 98:78152, Abstract of JP 57185219, "Antitumor benzophenone derivatives", Nov. 15, 1982.

Caplus 72:79046, Abstract of CH 479557, "Tuberculostatoic and cancerostatic polybasic ureas", Dr. A. Wander, Oct. 15, 1969.

Caplus 125:245169, "Production of murine monoclonal antibodies against sulcofuro and flucofuron by in vitro immunization", G. A. Bonwick et al., J. Immunol. Methods, pp. 163-173, 1996.

Caplus 127:34137f, "Preparation of quinoline an dquinazoline derivatives inhibiting platelet-derived growth factor receptor autophosphorylation", Kazuo Kubo et al., May 15, 1997.

Caplus 131:58658, "Inhibition of raf kinase using symmetrical and unsymmetrical substituted diphenyl ureas", Miller, Scott, Jul. 1, 1999.

Caplus 131:87909y, "Inhibition of p38 kinase activity using substituted heterocyclic ureas", Jacques Dumas, Jul. 1, 1999.

Caplus 131:73649b, "Preparation of pyrazolyl aryl ureas and related compounds as p38kinase inhibitor", Jacques Dumas, Jul. 1, 1999.

Joseph V. Simone, "Cecil Textbook of Medicine", 20th Edition, vol. 1, 2-3-1997. pp. 1004-1010.

Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.

Jacqueline E. van Muijlwijk-Koezen et al., "Isoquinoline and Quinazoline Urea Analogues as Antagonists for the Human Adenosine $A_3$ Receptor", J. Ed. Chem. 2000, 43, pp. 2227-2238, Jan. 3, 2000.

Jacques Dumas et al., "1-Phenyl-5-pyrazolyl Ureas: Potent and Selective p38 Kinase Inhibitors", Bioorganic & Medicianl Chemistry Letters, pp. 2051-2054, May 2, 2000.

Robert W. Carling et al., "1-(3-Cyanobenxylpiperidin-4-yl)-5-methyl-4-phenyl-1,3-dihydroimidazol-2-one: A Selective High-Affinity Antagonist for the Human Dopamine $D_4$ Receptor with Excellent Selectivity over Ion Channels", J. Med. Chem., 1999, 42, pp. 2706-2715.

Abstract WO 9822103, May 28, 1998, John Philip Hedge et al.

Abstract of DE 3305866A1, Aug. 29, 1984, Dr. Acker Rolf-Dieter et al.

Abstract of EP 4931(equivalent 4,240,820), K. Dickore e tal. (1980).

Dumas, J., "CAS Structure," May 6, 1997, pp. 1-29.

Scott,Bill, "Substructure (Patent Families)", Aug. 11, 1997, pp. 1-19.

Scott, Bill, "Substructure #2", Nov. 25, 1997, pp. 1-3.

"Beilstein number" Collection, 28 pages (1997).

"Beilstein Collection", 4 pages (1997).

Scott, Bill, "Substructure Search", Dec. 2, 1997, pp. 1-51.

Substucture Search, pp. 1-30. (1997).

Derwent World Patents Index Search, pp. 20-26. (1997).

Abstract of EP 116,932 (1984).

Abstract of EP 676,395 (1995).

Abstract of EP 202,538 (1986).

Abstract of EP 16,371 (1980).

* cited by examiner

INHIBITION OF RAF KINASE USING ARYL AND HETEROARYL SUBSTITUTED HETEROCYCLIC UREAS

This application is a continuation of Ser. No. 09/303,621 filed Dec. 22, 1998 now abandoned which claims priority of provisional application 60/135,502 filed Dec. 22, 1997.

FIELD OF THE INVENTION

This invention relates to the use of a group of aryl ureas in treating raf mediated diseases, and pharmaceutical compositions for use in such therapy.

BACKGROUND OF THE INVENTION

The $p21^{ras}$ oncogene is a major contributor to the development and progression of human solid cancers and is mutated in 30% of all human cancers (Bolton et al. *Ann. Rep. Med. Chem.* 1994, 29, 165-74; Bos. *Cancer Res.* 1989, 49, 4682-9). In its normal, unmutated form, the ras protein is a key element of the signal transduction cascade directed by growth factor receptors in almost all tissues (Avruch et al. *Trends Biochem. Sci.* 1994, 19, 279-83). Biochemically, ras is a guanine nucleotide binding protein, and cycling between a GTP-bound activated and a GDP-bound resting form is strictly controlled by ras' endogenous GTPase activity and other regulatory proteins. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants (Magnuson et al. *Semin. Cancer Biol.* 1994, 5, 247-53). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75).

SUMMARY OF THE INVENTION

The present invention provides compounds which are inhibitors of the enzyme raf kinase. Since the enzyme is a downstream effector of $p21^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine cancer, since the progression of these cancers is dependent upon the ras protein signal transduction cascade and therefore susceptible to treatment by interruption of the cascade, i.e., by inhibiting raf kinase. Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

The present invention, therefore, provides compounds generally described as aryl ureas, including both aryl and heteroaryl analogues, which inhibit the raf pathway. The invention also provides a method for treating a raf mediated disease state in humans or mammals. Thus, the invention is directed to compounds and methods for the treatment of cancerous cell growth mediated by raf kinase comprising administering a compound of formula I

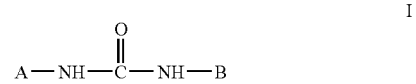

wherein B is generally an unsubstituted or substituted, up to tricyclic, aryl or heteroaryl moiety with up 30 carbon atoms with at least one 5 or 6 member aromatic structure containing 0-4 members of the group consisting of nitrogen, oxygen and sulfur. A is a heteroaryl moiety discussed in more detail below.

The aryl and heteroaryl moiety of B may contain separate cyclic structures and can include a combination of aryl, heteroaryl and cycloalkyl structures. The substituents for these aryl and heteroaryl moieties can vary widely and include halogen, hydrogen, hydrosulfide, cyano, nitro, amines and various carbon-based moieties, including those which contain one or more of sulfur, nitrogen, oxygen and/or halogen and are discussed more particularly below.

Suitable aryl and heteroaryl moieties for B of formula I include, but are not limited to, aromatic ring structures containing 4-30 carbon atoms and 1-3 rings, at least one of which is a 5-6 member aromatic ring. One or more of these rings may have 1-4 carbon atoms replaced by oxygen, nitrogen and/or sulfur atoms.

Examples of suitable aromatic ring structures include phenyl, pyridinyl, naphthyl, pyrimidinyl, benzothiozolyl, quinoline, isoquinoline, phthalimidinyl and combinations thereof, such as diphenyl ether (phenyloxyphenyl), diphenyl thioether (phenylthiophenyl), diphenyl amine (phenylaminophenyl), phenylpyridinyl ether (pyridinyloxyphenyl), pyridinylmethylphenyl, phenylpyyridinyl thioether (pyridinylthiophenyl), phenylbenzothiazolyl ether (benzothiazolyoxyphenyl), phenylbenzothiazolyl thioether (benzothiazolylthiophenyl), phenylpyrimidinyl ether, phenylquinoline thioether, phenylnaphthyl ether, pyridinylnapthyl ether, pyridinylnaphthyl thioether, and phthalimidylmethylphenyl.

Examples of suitable heteroaryl groups include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms.

For example, B can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methylphenyl, 5-methyl-2-thienyl, 4-methyl-2-thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc., throughout include methyl, ethyl, propyl, butyl, etc., including all straight-chain and branched isomers such as isopropyl, isobutyl, sec-butyl, tert-butyl, etc.

Suitable aryl groups include, for example, phenyl and 1- and 2-naphthyl.

Suitable cycloalkyl groups include cyclopropyl, cyclobutyl, cyclohexyl, etc. The term "cycloalkyl", as used herein, refers to cyclic structures with or without alkyl substituents such that, for example, "$C_4$ cycloalkyl" includes methyl substituted cyclopropyl groups as well as cyclobutyl groups. The term "cycloalkyl" also includes saturated heterocycles.

Suitable halogens include F, Cl, Br, and/or I, from one to persubstitution (i.e., all H atoms on the group are replaced by halogen atom), being possible, mixed substitution of halogen atom types also being possible on a given moiety.

As indicated above, these ring systems can be unsubstituted or substituted by substituents such as halogen up to per-halosubstitution. Other suitable substituents for the moieties of B include alkyl, alkoxy, carboxy, cycloalkyl, aryl, heteroaryl, cyano, hydroxy and amine. These other substituents, generally referred to as X and X' herein, include —N, —$CO_2R^5$, —$C(O)NR^5R^{5'}$, —$C(O)R^5$, —$NO_2$, —$OR^5$, —$SR^5$, —$NR^5R^{5'}$, —$NR^5C(O)OR^{5'}$, —$NR^5C(O)R^{5'}$, $C_1$-$C_{10}$ alkyl, $C_{2-10}$-alkenyl, $C_{1-10}$-alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_{2-10}$-alkenyl, substituted $C_{2-10}$-alkoxy, substituted $C_3$-$C_{10}$ cycloalkyl, substituted $C_4$-$C_{23}$ alkheteroaryl and —M—$L^1$.

Where a substituent, X or X', is a substituted group, it is preferably substituted by one or more substituents independently selected from the group consisting of —CN, —$CO_2R^5$, —$C(O)R^5$, —$C(O)NR^5R^{5'}$, —$OR^5$, —$SR^5$, —$NR^5R^{5'}$, —$NO_2$, —$NR^5C(O)R^{5'}$, —$NR^5C(O)OR^{5'}$ and halogen up to per-halo substitution.

The moieties $R^5$ and $R^{5'}$ are preferably independently selected from H, $C_1$-$C_{10}$ alkyl, $C_{2-10}$-alkenyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_{2-10}$-alkenyl up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl.

The bridging group M is preferably —O—, —S—, —N($R^5$)—, —($CH_2$)$_m$—, —C(O)—, —CH(OH)—, —$NR^5C(O)NR^5R^{5'}$—, —$NR^5C(O)$—, —$C(O)NR^5$—, —($CH_2$)$_m$O—, —($CH_2$)$_m$—, —($CH_2$)$_mN(R^5)$—, —O($CH_2$)$_m$—, —$CHX^a$—, —$CX^a{}_2$—, —S—($CH_2$)$_m$— and —N($R^5$)($CH_2$)$_m$—, where m=1-3, and $X^a$ is halogen.

The moiety L is preferably a 5-10 member aromatic structure containing 0-2 members of the group consisting of nitrogen, oxygen and sulfur which is unsubstituted or substituted by halogen up to per-halosubstitution and optionally substituted by $Z_{n1}$, wherein n1 is 0 to 3.

Each Z substituent is preferably independently selected from the group consisting of —CN, —$CO_2R^5$, —$C(O)NR^5R^{5'}$, —C(O)—$NR^5$, —$NO_2$, —$OR^5$, —$SR^5$, —$NR^5R^{5'}$, —$NR^5C(O)OR^{5'}$, —$C(O)R^5$, —$NR^5C(O)R^{5'}$, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, substituted $C_1$-$C_{10}$ alkyl, substituted $C_3$-$C_{10}$ cycloalkyl, substituted $C_7$-$C_{24}$ alkaryl and substituted $C_4$-$C_{23}$ alkheteroaryl. If Z is a substituted group, it is substituted by one or more substituents independently selected from the group consisting of —CN, —$CO_2R^5$, —$C(O)NR^5R^{5'}$, —$OR^5$, —$SR^5$, —$NO_2$, —$NR^5R^{5'}$, —$NR^5C(O)R^{5'}$ and —$NR^5C(O)OR^{5'}$.

The aryl and heteroaryl moieties of B of Formula I are preferably selected from the group consisting of

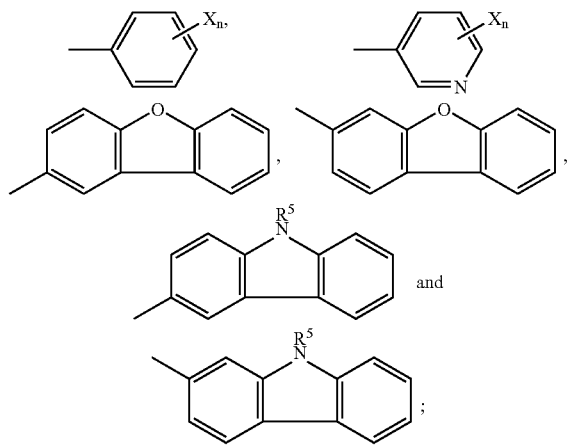

which are unsubstituted or substituted by halogen, up to per-halosubstitution. X is as defined above and n=0-3.

The aryl and heteroaryl moieties of B are more preferably of the formula:

wherein M is selected from the group consisting of —O—, —S—, —$CH_2$—, —$SCH_2$—, —$CH_2S$—, —CH(OH)—, —C(O)—, —$CX^a{}_2$, —$CX^aH$—, —$CH_2O$— and —$OCH_2$— and $X^a$ is halogen.

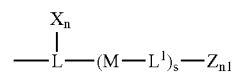

L is a six member aromatic structure containing 0-2 nitrogen, substituted or unsubstituted by halogen, up to per-halosubstitution and $L^1$ is a mono- or bicyclic aromatic structure of 3 to 10 carbon atoms and 0-4 members of the group consisting of N, O and S, unsubstituted or unsubstituted by halogen up to per-halosubstitution. X, Z, n and n1 are as defined above, and s=0 or 1.

In preferred embodiments, L is phenyl or pyridinyl, substituted or unsubstituted by halogen, up to per-halosubstitution and $L^1$ is selected from the group consisting of phenyl, pyridinyl, naphthyl, pyrimidinyl, quinoline, isoquinoline, imidazole and benzothiazolyl, substituted or unsubstituted by halogen, up to per-halo substitution, or —M—$L^1$ is phthalimidinyl substituted or unsubstituted by halogen up to per-halo substitution. Z and X are preferably independently selected from the group consisting of —$R^6$, —$OR^6$ and —$NHR^7$, wherein $R^6$ is hydrogen, $C_1$-$C_{10}$-alkyl or $C_3$-$C_{10}$-cycloalkyl and $R^7$ is preferably selected from the group consisting of hydrogen, $C_3$-$C_{10}$-alkyl, $C_3$-$C_6$-cycloalkyl and $C_6$-$C_{10}$-aryl, wherein $R^6$ and $R^7$ can be substituted by halogen or up to per-halosubstitution.

The heteroaryl moiety A of formula I is preferably selected from the group consisting of

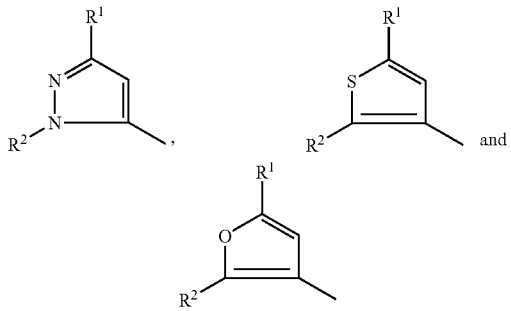

wherein $R^1$ is preferably selected from the group consisting of $C_3$-$C_{10}$ alkyl, $C_3$-$C_{10}$ cycloalkyl, up to per-halosubstituted $C_1$-$C_{10}$ alkyl and up to per-halosubstituted $C_3$-$C_{10}$ cycloalkyl and $R^2$ is $C_6$-$C_{14}$ aryl, $C_3$-$C_{14}$ heteroaryl, substituted $C_6$-$C_{14}$ aryl or substituted $C_3$-$C_{14}$ heteroaryl.

Where $R^2$ is a substituted group, the substituents are preferably independently selected from the group consisting of halogen, up to per-halosubstitution, and $V_n$, where n=0-3.

Each V is preferably independently selected from the group consisting of —CN, —OC(O)$NR^5R^{5'}$, —$CO_2R^5$, —C(O)$NR^5R^{5'}$, —$OR^5$, —$SR^5$, —$NR^5R^{5'}$, —C(O)$R^5$, —$NR^5C(O)OR^{5'}$; —$SO_2R^5$, —$SOR^5$, —$NR^5C(O)R^{5'}$, —$NO_2$, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{24}$ alkheteroaryl, substituted $C_1$-$C_{10}$ alkyl, substituted $C_3$-$C_{10}$ cycloalkyl, substituted $C_6$-$C_{14}$ aryl, substituted $C_3$-$C_{13}$ heteroaryl, substituted $C_7$-$C_{24}$ alkaryl and substituted $C_4$-$C_{24}$ alkheteroaryl.

If V is a substituted group, it is preferably substituted by one or more substituents independently selected from the group consisting of halogen, up to per-halosubstitution, —CN, —$CO_2R^5$, —C(O)$R^5$, —C(O)$NR^5R^{5'}$, —$NR^5R^{5'}$, —$OR^5$, —$SR^5$, —$NR^5C(O)R^{5'}$, —$NR^5C(O)OR^{5'}$ and —$NO_2$.

The substituents $R^5$ and $R^{5'}$ are preferably each independently selected form the group consisting of H, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl.

$R^2$ is preferably substituted or unsubstituted phenyl or pyridinyl, where the substituents for $R^2$ are selected from the group consisting of halogen, up to per-halosubstitution and $V_n^1$, wherein n=0-3. Each $V^1$ is preferably independently selected from the group consisting of substituted and unsubstituted $C_1$-$C_6$ alkyl, $C_3$-$C_{10}$ cycloalkyl, $C_6$-$C_{10}$ aryl, —$NO_2$, —$NH_2$, —C(O)—$C_{1-6}$ alkyl, —C(O)N—$(C_{1-6}$ alkyl)$_2$, —C(O)NH—$C_{1-6}$ alkyl, —O—$C_{1-6}$ alkyl, —NHC(O)H, —NHC(O)OH, —N($C_{1-6}$ alkyl)C(O)—$C_{1-6}$ alkyl, —N—($C_{1-6}$ alkyl)C(O)—$C_{1-6}$ alkyl, —NHC(O)—$C_{1-6}$ alkyl, —OC(O)NH—$C_{6-14}$, —NHC(O)O—$C_{1-6}$ alkyl, —S(O)—$C_{1-6}$ alkyl and —$SO_2$—$C_{1-6}$ alkyl. Where $V^1$ is a substituted group, it is preferably substituted by one or more halogen, up to per-halosubstitution.

Most preferably, $R^2$ is selected from substituted and unsubstituted phenyl or pyridinyl groups, where the substituents are halogen and $W_n$ (n=0-3).

W is preferably selected from the group consisting of —$NO_2$, —$C_{1-3}$ alkyl, —NH(O)$CH_3$, —$CF_3$, —$OCH_3$, —F, —Cl, —$NH_2$, —OC(O)NH— up to per-halo substituted phenyl, —$SO_2CH_3$, pyridinyl, phenyl, up to per-halosubstituted phenyl and $C_1$-$C_6$ alkyl substituted phenyl.

The invention also relates the compounds within the scope of general formula I described above. These more particularly include pyrazolyl ureas of the formula

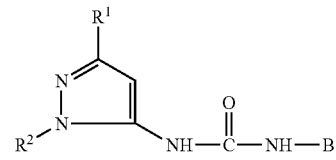

furyl ureas of the formula

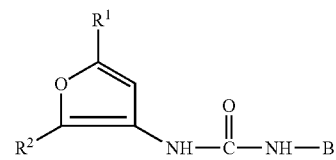

and thienyl ureas of the formula

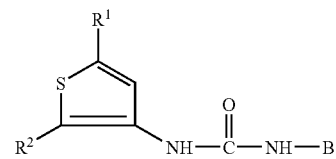

wherein $R^1$, $R^2$ and B are as defined above.

The present invention is also directed to pharmaceutically acceptable salts of formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, sulphonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations such as those arising from protonation or peralkylation of triethylamine, N,N-diethylamine, N,N-dicyclohexylamine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo [5.4.0]undec-7-ene (DBU).

The compounds of Formula I may be prepared by use of known chemical reactions and procedures. Nevertheless, the following general preparative methods are presented to aid one of skill in the art in synthesizing the inhibitors, with more detailed examples being presented in the experimental section describing the working examples.

General Preparative Methods

Heterocyclic amines may be synthesized utilizing known methodology (Katritzky, et al. *Comprehensive Heterocyclic Chemistry*; Permagon Press: Oxford, UK (1984). March. *Advanced Organic Chemistry*, 3$^{rd}$ Ed.; John Wiley: New York (1985)). For example, as shown in Scheme 1,5-aminopyrazoles substituted at the N–1 position with either aryl or heteroaryl moieties may be synthesized by the reaction of an α-cyanoketone (2) with the appropriate aryl- or heteroaryl hydrazine (3, $R^2$=aryl or heteroaryl). Cyanoketone 2, in turn, is available from the reaction of acetamidate ion with an appropriate acyl derivative, such as an ester, an acid halide, or an acid anhydride. In cases where the $R^2$ moiety offers suitable anion stabilization, 2-aryl- and 2-heteroarylfurans may be synthesized from a Mitsunobu reaction of cyanoketone 2 with alcohol 5, followed by base catalyzed cyclization of enol ether 6 to give furylamine 7.

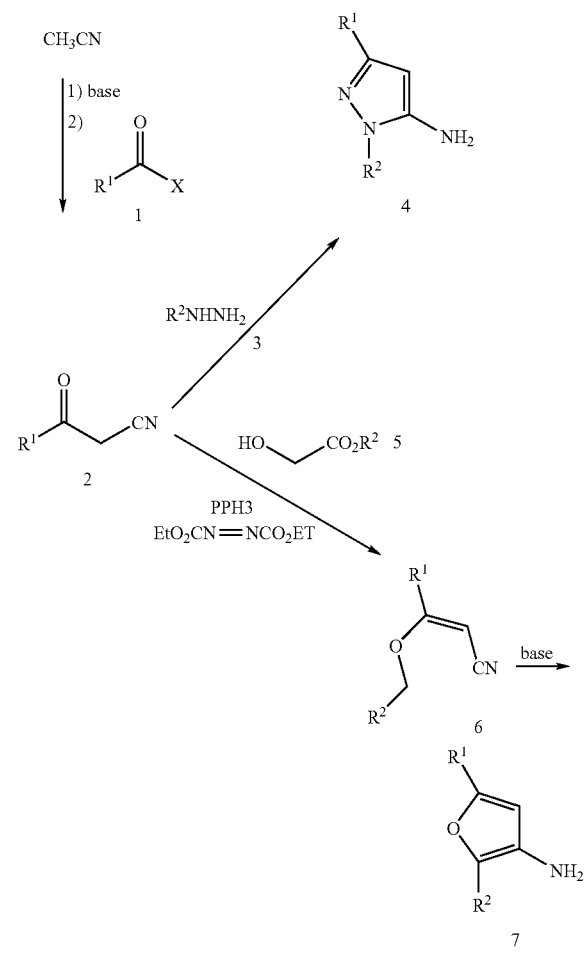

Scheme I. Selected General Methods for Heterocyclic Amine Synthesis

Substituted anilines may be generated using standard methods (March. *Advanced Organic Chemistry*, 3$^{rd}$ Ed.; John Wiley: New York (1985). Larock. *Comprehensive Organic Transformations*; VCH Publishers: New York (1989)). As shown in Scheme II, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3$^{rd}$ Ed.; John Wiley: New York (1985). Larock. *Comprehensive Organic Transformations*; VCH Publishers: New York (1989)).

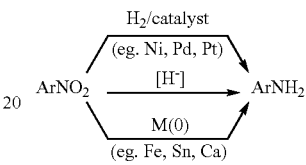

Scheme II Reduction of Nitroaryls to Aryl Amines

Nitroaryls are commonly formed by electrophilic aromatic nitration using $HNO_3$, or an alternative $NO_2^+$ source. Nitro aryls may be further elaborated prior to reduction. Thus, nitroaryls substituted with

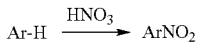

potential leaving groups (eg. F, Cl, Br, etc.) may undergo substitution reactions on treatment with nucleophiles, such as thiolate (exemplified in Scheme III) or phenoxide. Nitroaryls may also undergo Ullman-type coupling reactions (Scheme III).

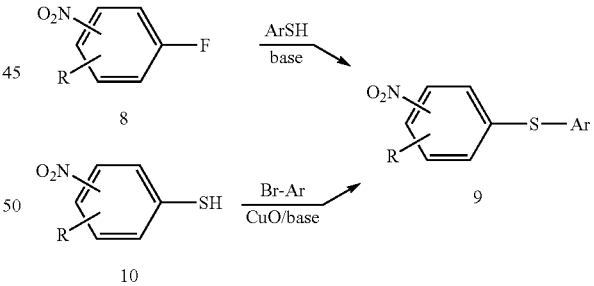

Scheme III Selected Nucleophilic Aromatic Substitution Using Nitroaryls

As shown in Scheme IV, urea formation may involve reaction of a heteroaryl isocyanate (12) with an aryl amine (11). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent. A urea may also be generated from the reaction of an aryl isocyanate (15) with a heterocyclic amine.

thiophenecarboxylate 21 (Ishizaki et al. JP 6025221). Decarboxylation of ester 21 may be achieved by protection of the amine, for example as the tert-butoxy (BOC) carbamate (22), followed by saponification and treatment with acid. When BOC protection is used, decarboxylation may be accompanied by deprotection giving the substituted

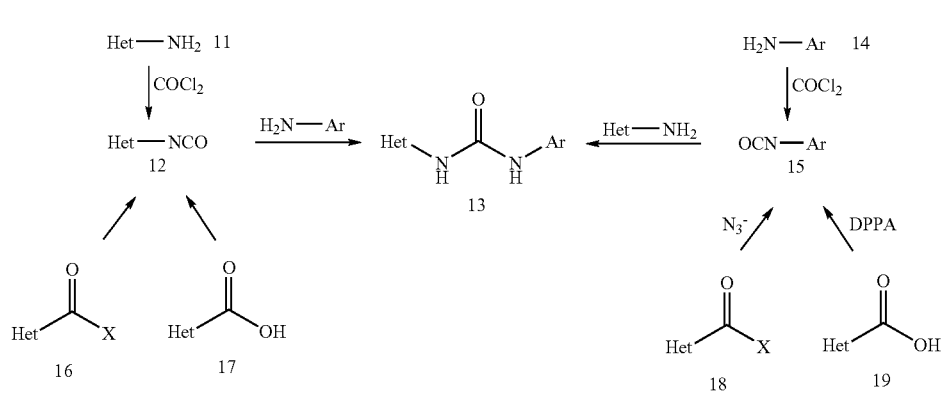

Scheme IV Selected Methods of Urea Formation (Het=heterocycle)

Finally, ureas may be further manipulated using methods familiar to those skilled in the art. For example, 2-aryl and 2-heteroarylthienyl ureas are available from the corresponding 2-halothienyl urea through transition metal mediated cross coupling reactions (exemplified with 2-bromothiophene 25, Scheme V). Thus, reaction of nitrile 20 with an α-thioacetate ester gives 5-substituted-3-amino-2-

3-thiopheneammonium salt 23. Alternatively, ammonium salt 23 may be directly generated through saponification of ester 21 followed by treatment with acid. Following urea formation as described above, bromination affords penultimate halothiophene 25. Palladium mediated cross coupling of thiophene 25 with an appropriate tributyl- or trimethyltin ($R^2$=aryl or heteroaryl) then affords the desired 2-aryl- or 2-heteroarylthienyl urea.

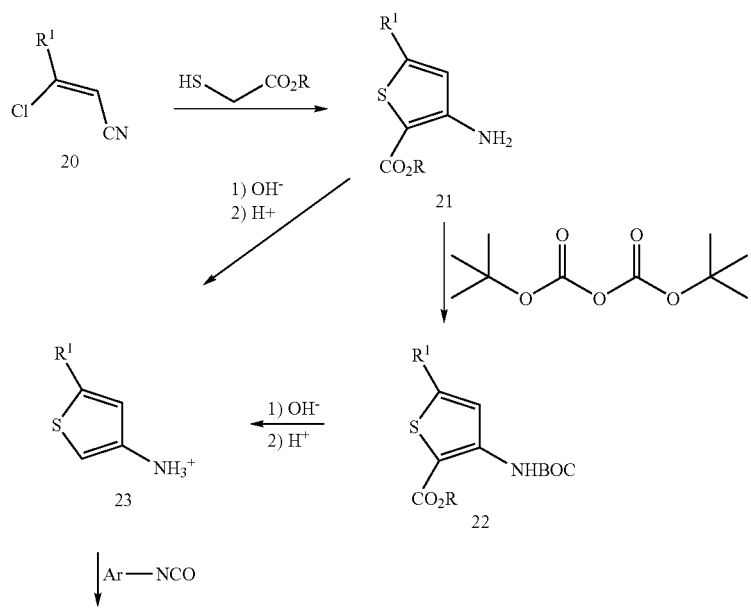

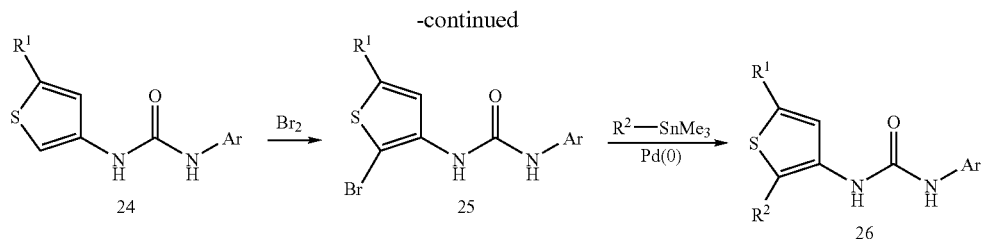

The invention also includes pharmaceutical compositions including a compound of Formula I, and a physiologically acceptable carrier.

The compounds may be administered orally, topically, parenterally, by inhalation or sprays vaginally, sublingually, or rectally in dosage unit formulations. The term 'administration by injection' includes intravenous, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administrated transdermally using methods known to those skilled in the art (see, for example: Chien: "Transdermal Controlled Systemic Medications": Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily vaginal dosage regimen will preferably be from 0.01 to 200 mg/Kg of total body weight. The daily rectal dosage regime will preferably be from 0.01 to 200 mg/Kg of total body weight. The daily topical dosage regime will preferably be from 0.1 to 200 mg administered between one to four times daily. The transdermal concentration will preferably be that required to maintain a daily dose of from 0.01 to 200 mg/Kg. The daily inhalation dosage regime will preferably be from 0.01 to 10 mg/Kg of total body weight.

It will be appreciated by those skilled in the art that the particular method of administration will depend on a variety of factors, all of which are considered routinely when administering therapeutics. It will also be appreciated by one skilled in the art that the specific dose level for any given patient will depend upon a variety of factors, including, the activity of the specific compound administered, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the condition undergoing therapy.

The entire disclosure of all applications, patents and publications cited above and below are hereby incorporated by reference, including provisional application Ser. No. 60/135,502, filed on Dec. 22, 1997 as Ser. No. 08/996,181 converted on Dec. 22, 1998.

The compounds are producible from known compounds (or from starting materials which, in turn, are producible from known compounds), e.g., through the general preparative methods shown below. The activity of a given compound to inhibit raf kinase can be routinely assayed, e.g., according to procedures disclosed below. The following examples are for illustrative purposes only and are not intended, nor should they be construe to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg.

All temperatures are reported uncorrected in degrees Celsius (° C.). Unless otherwise indicated, all parts and percentages are by weight.

Commercial grade reagents and solvents were used without further purification. Thin-layer chromatography (TLC) was performed on Whatman® pre-coated glass-backed silica gel 60A F-254 250 µm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Proton ($^1$H) nuclear magnetic resonance (NMR) spectra were measured with a General Electric GN-Omega 300 (300 MHz) spectrometer with either Me$_4$Si (0.00) or residual protonated solvent (CHCl$_3$ 7.26; MeOH 3.30; DMSO 2.49) as standard. Carbon ($^{13}$C) NMR spectra were measured with a General Electric GN-Omega 300 (75 MHz) spectrometer with solvent (CDCl$_3$ 77.0; MeOD-d$_3$; 49.0; DMSO-d$_6$ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 µA. Liquid-cesium secondary ion mass spectra (FAB-MS), an updated version of fast atom bombardment were obtained using a Kratos Concept 1-H spectrometer. Chemical ionization mass spectra (CI-MS) were obtained using a Hewlett Packard MS-Engine (5989A) with methane as the reagent gas (1×10$^{-4}$ torr to 2.5×10$^{-4}$ torr). The direct insertion desorption chemical ionization (DCI) probe (Vacumetrics, Inc.) was ramped from 0-1.5 amps in 10 sec and held at 10 amps until all traces of the sample disappeared (~1-2 min). Spectra were scanned from 50-800 amu at 2 sec per scan. HPLC-electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source. Gas chromatography-ion selective mass spectra (GC-MS) were obtained with a Hewlett Packard 5890 gas chromatograph equipped with an HP-1 methyl silicone column (0.33 M coating; 25 m×0.2 mm) and a Hewlett Packard 5971 Mass Selective Detector (ionization energy 70 eV).

Elemental analyses were conducted by Robertson Microlit Labs, Madison N.J. All ureas displayed NMR spectra, LRMS and either elemental analysis or HRMS consistant with assigned structures.

| List of Abbreviations and Acronyms: | |
|---|---|
| AcOH | acetic acid |
| anh | anhydrous |
| BOC | tert-butoxycarbonyl |
| conc | concentrated |
| dec | decomposition |
| DMPU | 1,3-dimethyl-3,4,5,6-tetrahydro-2(1H)-pyrimidinone |
| DMF | N,N-dimethylformamide |
| DMSO | dimethylsulfoxide |
| DPPA | diphenylphosphoryl azide |
| EtOAc | ethyl acetate |
| EtOH | ethanol (100%) |
| Et$_2$O | diethyl ether |
| Et$_3$N | triethylamine |

| -continued | |
|---|---|
| List of Abbreviations and Acronyms: | |
| m-CPBA | 3-chloroperoxybenzoic acid |
| MeOH | methanol |
| pet. ether | petroleum ether (boiling range 30-60° C.) |
| THF | tetrahydrofuran |
| TFA | trifluoroacetic acid |
| Tf | trifluoromethanesulfonyl |

A. General Methods for Synthesis of Heterocyclic Amines

A1. General Procedure for the Preparation of N'-Aryl-5-aminopyrazoles

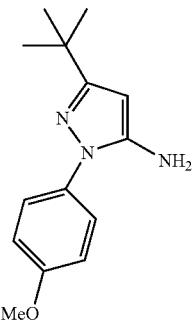

N'-(4-Methoxyphenyl)-5-amino-3-tert-butylpyrazole: A mixture of 4-methoxyphenylhydrazine hydrochloride (3.5 g), 4,4-dimethyl-3-oxopentanenitrile (2.5 g), EtOH (30 mL), and AcOH (1 mL) was heated at the reflux temperature for 3 h, cooled to room temp., and poured into a mixture of EtO (100 mL) and a 10% Na$_2$CO$_3$ solution (100 mL). The organic layer was washed with a saturated NaCl solution, dried (MgSO$_4$) and concentrated under reduced pressure. The solid residue was washed with pentane to afford the desired pyrazole as a pale brown solid. (4.25 g): $^1$H-NMR (DMSO-d$_6$) δ 1.18 (s, 9H); 3.78 (s, 3H); 5.02 (br s, 2H); 5.34 (s, 1H); 6.99 (d, J=8 Hz, 2H); 7.42 (d, J=8 Hz, 2H).

A2. General Method for the Mitsunobu-Based Synthesis of 2-Aryl-3-aminofurans

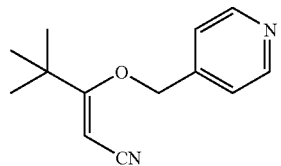

Step 1. 4,4-Dimethyl-3-(4-pyridinylmethoxy)-2-pentenenitrile: A solution of triphenylphosphine (2.93 g, 11.2 mmol) in anh THF (50 mL) was treated with diethyl azodicarboxylate (1.95 g, 11.2 mmol) and 4-pyridinylmethanol (1.22 g, 11.2 mmol), then stirred for 15 min. The resulting white slurry was treated with 4,4-dimethyl-3-oxopentanenitrile (1.00 g, 7.99 mmol), then stirred for 15 min. The reaction mixture was concentrated under reduced pressure. The residue was purified by column chromatography (30% EtOAc/70% hexane) to give the desired nitrile as a yellow solid (1.83 g, 76%): TLC (20% EtOAc/80% hexane) $R_f$ 0.13; $^1$H-NMR (CDCl$_3$) δ1.13 (s, 9H), 4.60 (s, 1H), 5.51 (s, 2H), 7.27 (d, J=5.88 Hz, 2H), 8.60 (d, J6.25 Hz, 2H); $^{13}$C-NMR (CDCl$_3$) δ 27.9 (3C), 38.2, 67.5, 70.8, 117.6, 121.2 (2C), 144.5, 149.9 (2C), 180.7; CI-MS m/z (rel abundance) 217 ((M+H)$^+$, 100%).

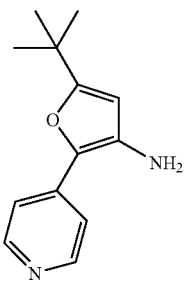

Step 2. 3-Amino-2-(4-pyridinyl)-5-tert-butylfuran: A solution of 4,4-dimethyl-3-(4-pyridinylmethoxy)-2-pentenenitrile (1.55 g, 7.14 mmol) in anh DMSO (75 mL) was treated with potassium tert-butoxide (0.88 g, 7.86 mmol) and stirred at room temp for 10 min. The resulting mixture was treated with EtOAc (300 mL), then sequentially washed with water (2×200 mL) and a saturated NaCl solution (100 mL). Combined aqueous phases were back-extracted with EtOAc (100 mL). The combined organic phases were dried (Na$_2$SO$_4$) and concentrated under reduced pressure. The residue was purified by column chromatography (gradient from 30% EtOAc/70% hexane to 100% EtOAc) to give the desired product as an orange oil (0.88 g, 57%): TLC (40% EtOAc/60% hexane) $R_f$ 0.09; $^1$H-NMR (CDCl$_3$) δ 1.28 (s, 9H), 3.65 (br s, 2H), 5.79 (s, 1H), 7.30 (d, J=6.25 Hz, 2H), 8.47 (d, J=6.25 Hz, 2H); EI-MS m/z (rel abundance) 216 (M, 30%).

A3. Synthesis 3-Amino-5-alkylthiophenes from N—BOC 3-Amino-5-alkyl-2-thiophenecarboxylate esters

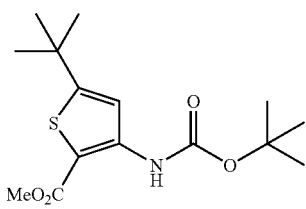

Step 1. Methyl 3-(tert-Butoxycarbonylamino)-5-tert-butyl-2-thiophenecarboxy-late: To a solution of methyl 3-amino-5-tert-butyl-2-thiophenecarboxylate (150 g, 0.70 mol) in pyridine (2.8 L) at 5° C. was added di-tert-butyl dicarbonate (171.08 g, 0.78 mol, 1.1 equiv) and N,N-dimethylaminopyridine (86 g, 0.70 mol, 1.00 equiv) and the resulting mixture was stirred at room temp for 7 d. The resulting dark solution was concentrated under reduced pressure (approximately 0.4 mmHg) at approximately 20° C. The resulting red solids were dissolved in CH$_2$Cl$_2$ (3 L) and sequentially washed with a 1 M H$_3$PO$_4$ solution (2×750 ml), a saturated NaHCO$_3$ solution (800 mL) and a saturated NaCl solution (2×800 mL), dried (Na$_2$SO$_4$) and concentrated under reduced pressure. The resulting orange solids were dissolved in abs. EtOH (2 L) by warming to 49° C., then treated with water (500 mL) to afford the desired product as an off-white solid (163 g, 74%): $^1$H-NMR (CDCl$_3$) δ 1.38 (s, 9H), 1.51 (s, 9H), 3.84 (s, 3H), 7.68 (s, 1H), 9.35 (br s, 1H); FAB-MS m/z (rel abundance) 314 ((M+H)$^+$, 45%).

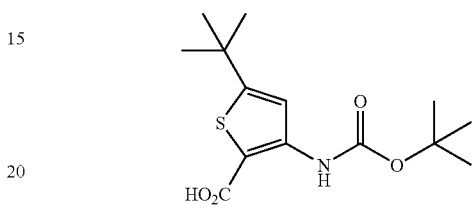

Step 2. 3-(tert-Butoxycarbonylamino)-5-tert-butyl-2-thiophenecarboxylic Acid: To a solution of methyl 3-(tert-butoxycarbonylamino)-5-tert-butyl-2-thiophenecarboxylate (90.0 g, 0.287 mol) in THF (630 mL) and MeOH (630 mL) was added a solution of NaOH (42.5 g, 1.06 mL) in water (630 mL). The resulting mixture was heated at 60° C. for 2 h, concentrated to approximately 700 mL under reduced pressure, and cooled to 0° C. The pH was adjusted to approximately 7 with a 1.0 N HCl solution (approximately 1 L) while maintaining the internal temperature at approximately 0° C. The resulting mixture was treated with EtOAc (4 L). The pH was adjusted to approximately 2 with a 1.0 N HCl solution (500 mL). The organic phase was washed with a saturated NaCl solution (4×1.5 L), dried (Na$_2$SO$_4$), and concentrated to approximately 200 mL under reduced pressure. The residue was treated with hexane (1 L) to form a light pink solid (41.6 g). Resubmission of the mother liquor to the concentration-precipitation protocol afforded additional product (38.4 g, 93% total yield): $^1$H-NMR (CDCl$_3$) δ 1.94 (s, 9H), 1.54 (s, 9H), 7.73 (s, 1H), 9.19 (br s, 1H); FAB-MS m/z (rel abundance) 300 ((M+H)$^+$, 50%).

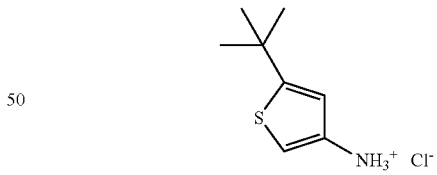

Step 3. 5-tert-Butyl-3-thiopheneammonium Chloride: A solution of 3-(tert-butoxycarbonylamino)-5-tert-butyl-2-thiophenecarboxylic acid (3.0 g, 0.010 mol) in dioxane (20 mL) was treated with an HCl solution (4.0 M in dioxane, 12.5 mL, 0.050 mol, 5.0 equiv), and the resulting mixture was heated at 80° C. for 2 h. The resulting cloudy solution was allowed to cool to room temp forming some precipitate. The slurry was diluted with EtOAc (50 mL) and cooled to −20° C. The resulting solids were collected and dried overnight under reduced pressure to give the desired salt as an off-white solid (1.72 g, 90%): $^1$H-NMR (DMSO-d$_6$) δ 1.31 (s, 9H), 6.84 (d, J=1.48 Hz, 1H), 7.31 (d, J=1.47 Hz, 1H), 10.27 (br s, 3H).

B. General Methods for Synthesis of Substituted Anilines

B1. General Method for Substituted Aniline Synthesis Via Nucleophilic Aromatic Substitution Using a Halopyridine

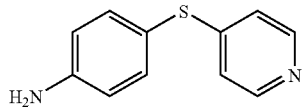

3-(4-Pyridinylthio)aniline: To a solution of 3-aminothiophenol (3.8 mL, 34 mmoles) in anh DMF (90 mL) was added 4-chloropyridine hydrochloride (5.4 g, 35.6 mmoles) followed by $K_2CO_3$ (16.7 g, 121 mmoles). The reaction mixture was stirred at room temp. for 1.5 h, then diluted with EtOAc (100 mL) and water (100 mL). The aqueous layer was back-extracted with EtOAc (2×100 mL). The combined organic layers were washed with a saturated NaCl solution (100 mL), dried ($MgSO_4$), and concentrated under reduced pressure. The residue was filtered through a pad of silica (gradient from 50% EtOAc/50% hexane to 70% EtOAc/30% hexane) and the resulting material was triturated with a $Et_2O$/hexane solution to afford the desired product (4.6 g, 66%): TLC (100% ethyl acetate) $R_f$ 0.29; $^1$H-NMR (DMSO-$d_6$) δ 5.41 (s, 2H), 6.64-6.74 (m, 3H), 7.01 (d, J=4.8, 2H), 7.14 (t, J=7.8 Hz, 1H), 8.32 (d, J=4.8, 2H).

C. General Methods of Urea Formation

C1a. Reaction of a Heterocyclic Amine with an Aryl Isocyanate

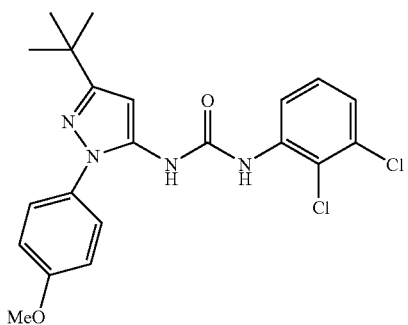

N-(1-(4-Methoxyphenyl)-3-tert-butyl-5-pyrazolyl)-N'-(2,3-dichlorophenyl)urea: To a stirring solution of 1-(4-methoxyphenyl)-3-tert-butyl-5-aminopyrazole (0.342 g, 1.39 mmol) in anh toluene (9 mL) was added 2,3-dichlorophenyl isocyanate (0.276 mL, 2.09 mmol). The solution was sealed and stirred in the dark for 96 h at 60° C. After this time, the reaction mixture was diluted with EtOAc (200 mL). The resulting mixture was sequentially washed with a 1 M HCl solution (2×125 mL) and a saturated NaCl solution (50 mL), dried ($MgSO_4$), and concentrated under reduced pressure. The residue was purified by column chromatography (20% EtOAc/80% hexane) to give the product as a white solid (0.335 g, 56%): TLC (20% EtOAc/80% hexane) $R_f$ 0.22; $^1$H NMR (DMSO-$d_6$) δ 1.24 (s, 9H), 3.79 (s, 3H), 6.33 (s, 1H), 7.05 (d, J=9 Hz, 2H), 7.28 (m, 2H), 7.38 (d, J=9 Hz, 2H), 8.05 (dd, J=3, 6 Hz, 1H), 8.75 (s, 1H), 9.12 (s, 1H); FAB-MS m/z 433 ((M+H)$^+$).

C1b. Reaction of a Heterocyclic Amine with an Aryl Isocyanate

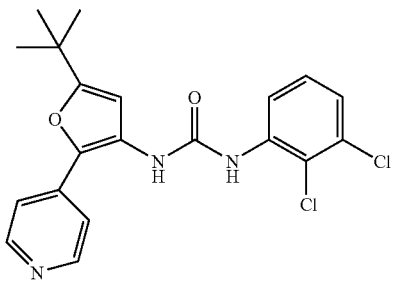

N-(2-(4-Pyridinyl)-5-tert-butyl-3-furyl)-N'-(2,3-dichlorophenyl)urea: A solution of 3-amino-2-(4-pyridinyl)-5-tert-butylfuran (Method A2; 0.10 g, 0.46 mmol) and 2,3-dichlorophenyl isocyanate (0.13 g, 0.69 mmol) in $CH_2Cl_2$ was stirred at room temp. for 2 h, then was treated with 2-(dimethylamino)ethylamine (0.081 g, 0.92 mmol) and stirred for an additional 30 min. The resulting mixture was diluted with EtOAc (50 mL), then was sequentially washed with a 1 N HCl solution (50 mL), a saturated $NaHCO_3$ solution (50 mL) and a saturated NaCl solution (50 mL), dried ($Na_2SO_4$), and concentrated under reduced pressure. The residue was purified using column chromatography (gradient from 10% EtOAc/90% hexane to 40% EtOAc/60% hexane) to give the desired compound as a white solid (0.12 g, 63%): mp 195-198° C.; TLC (60% EtOAc/40% hexane) $R_f$ 0.47; $^1$H NMR (DMSO-$d_6$) δ1.30 (s, 9H); 6.63 (s, 1H); 7.30-7.32 (m, 2H), 7.58 (dm, J=6.62 Hz, 2H), 8.16 (dd, J=2.57, 6.99 Hz, 1H), 8.60 (dm, J=6.25 Hz, 2H), 8.83 (s, 1H), 9.17 (s, 1H); $^{13}$C NMR (DMSO-$d_6$) δ 28.5 (3C), 32.5, 103.7, 117.3 (2C), 119.8, 120.4, 123.7, 125.6, 128.1, 131.6, 135.7, 136.5, 137.9, 150.0 (2C), 152.2, 163.5; CI-MS m/z (rel abundance) 404 ((M+H)$^+$, 15%), 406 ((M+H+2)$^+$, 8%).

C1c. Reaction of a Heterocyclic Amine with an Isocyanate

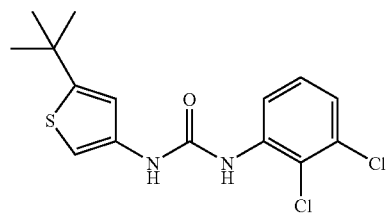

N-(5-tert-Butyl-3-thienyl)-N'-(2,3-dichlorophenyl)urea: Pyridine (0.163 mL, 2.02 mmol) was added to a slurry of 5-tert-butylthiopheneammonium chloride (Method A4c; 0.30 g, 1.56 mmol) and 2,3-dichlorophenyl isocyanate (0.32 mL, 2.02 mmol) in $CH_2Cl_2$ (10 mL) to clarify the mixture and the resulting solution was stirred at room temp. overnight. The reaction mixture was then concentrated under reduced pressure and the residue was separated between EtOAc (15 mL) and water (15 mL). The organic layer was sequentially washed with a saturated $NaHCO_3$ solution (15 mL), a 1N HCl solution (15 mL) and a saturated NaCl solution (15 mL), dried ($Na_2SO_4$), and concentrated under reduced pressure. A portion of the residue was treated by preparative HPLC (C-18 column; 60% acetonitrile/40% water/0.05% TFA) to give the desired urea (0.180 g, 34%): mp 169-170° C.; TLC (20% EtOAc/80% hexane) $R_f$ 0.57;

$^1$H-NMR (DMSO-d$_6$) δ 1.31 (s, 9H), 6.79 (s, 1H), 7.03 (s, 1H), 7.24-7.33 (m, 2H), 8.16 (dd, J=1.84, 7.72 Hz, 1H), 8.35 (s, 1H), 9.60 (s, 1H); $^{13}$C-NMR (DMSO-d$_6$) δ 31.9 (3C), 34.0, 103.4, 116.1, 119.3, 120.0, 123.4, 128.1, 131.6, 135.6, 138.1, 151.7, 155.2; FAB-MS m/z (rel abundance) 343 ((M+H)$^+$, 83%), 345 ((M+H+2)$^+$, 56%), 347 ((M+H+4)$^+$, 12%).

C2. Reaction of Substituted Aniline with N,N'-Carbonyldiimidazole Followed by Reaction with a Heterocyclic Amine

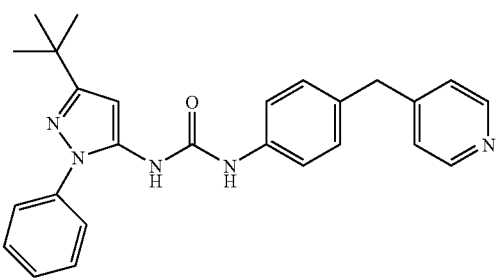

N-(1-Phenyl-3-tert-butyl-5-pyrazolyl)-N'-(4-(4-pyridinylmethyl)phenyl)urea: A solution of 4-(4-pyridinylmethyl)aniline (0.25 g, 1.38 mmol) and N,N'-carbonyldiimidazole (0.23 g, 1.42 mmol) in CH$_2$Cl$_2$ 11 mL) at room temp. was stirred for 2 h, then treated with 5-amino-1-phenyl-3-tert-butyl-5-pyrazole (0.30 g, 1.38 mmol) and the resulting mixture was stirred at 50° C. overnight. The reaction mixture was diluted with EtOAc (25 mL), then sequentially washed with water (30 mL) and a saturated NaCl solution (30 mL), dried (MgSO$_4$), and concentrated under reduced pressure. The residue was purified by column chromatography (gradient from 100% CH$_2$Cl$_2$ to 30% acetone/70% CH$_2$Cl$_2$) and the resulting material was recrystallized (EtOAc/Et$_2$O) to give the desired product complexed with 0.25 equiv H$_2$O (0.30 g): TLC (60% acetone/40% CH$_2$Cl$_2$) R$_f$ 0.56; $^1$H-NMR (DMSO-d$_6$) δ 1.25 (s, 9H); 3.86 (s, 2H), 6.34 (s, 1H), 7.11 (d, J=8.82 Hz, 2H), 7.19 (dm, J=6.25 Hz, 2H), 7.31 (d, J=1.84 Hz, 2H), 7.35-7.51 (m, 5H), 8.34 (s, 1H), 8.42 (dm, J=5.98 Hz, 2H), 8.95 (s, 1H); FAB-MS m/z (rel abundance) 426 ((M+H)$^+$, 100%).

D. Interconversion of Ureas

D1. General Method for Electrophylic Halogenation of Aryl Ureas

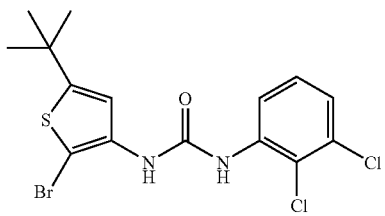

N-(2-Bromo-5-tert-butyl-3-thienyl)-N'-(2-3-dichlorophenyl)urea: To a slurry of N-(5-tert-butyl-3-thienyl)-N'-(2,3-dichlorophenyl)urea (Method C1c; 3.00 g, 8.74 mmol) in CHCl$_3$ (200 mL) at room temp was slowly added a solution of Br$_2$ (0.46 mL, 1.7 mmol) in CHCl$_3$ (150 mL) via addition funnel over 2.5 h, causing the reaction mixture to become homogeneous. Stirring was continued 20 min after which TLC analysis indicated complete reaction. The reaction mixture was concentrated under reduced pressure, and the residue triturated (Et$_2$O/hexane) and the resulting solids were washed (hexane) to give the brominated product as a pink powder (3.45 g, 93%): mp 180-183° C.; TLC (10% EtOAc/90% hexane) R$_f$ 0.68; $^1$H NMR (DMSO-d$_6$) δ 1.28 (s, 9H), 7.27-7.31 (m, 2H), 7.33 (s, 1H), 8.11 (dd, J=3.3, 6.6 Hz, 1H), 8.95 (s, 1H), 9.12 (s, 1H); $^{13}$C NMR (DMSO-d$_6$) δ31.5 (3C), 34.7, 91.1, 117.9, 120.1, 120.5, 123.8, 128.0, 131.6, 135.5, 137.9, 151.6, 155.3; FAB-MS m/z (rel abundance) 421 ((M+H)$^+$, 7%), 423 (M+2+H)$^+$, 10%).

D2. General Method for Metal-Mediated Cross-Coupling Reactions with Halogen-Substituted Ureas

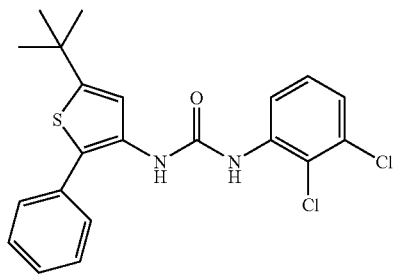

N-(2-Phenyl-5-tert-butyl-3-thienyl)-N'-(2,3-dichlorophenyl)urea: To a solution of N-(3-(2-bromo-5-tert-butylthienyl)-N'-(2,3-dichlorophenyl)urea (0.50 g, 1.18 mmol) and phenyltrimethyltin (0.21 mL, 1.18 mmol) in DMF (15 mL) was added Pd(PPh$_3$)$_2$Cl$_2$ (0.082 g, 0.12 mmol), and the resulting suspension was heated at 80° C. overnight. The reaction mixture was diluted with EtOAc (50 mL) and water (50 mL), and the organic layer sequentially washed with water (3×50 mL) and a saturated NaCl solution (50 mL), then dried (Na$_2$SO$_4$) and concentrated under reduced pressure. The residue was purified by MPLC (Biotage®; gradient from 100% hexane to 5% EtOAc/95% hexane) followed by preparative HPLC (C-18 column; 70% CH$_3$CN/30% water/0.05% TFA). The HPLC fractions were concentrated under reduced pressure and the resulting aqueous mixture was extracted with EtOAc (2×50 mL). The combined organic layers were dried (Na$_2$SO$_4$) and concentrated under reduced pressure to give a gummy semi-solid, which was triturated with hexane to afford the desired product as a white solid (0.050 g, 10%): mp 171-173° C.; TLC (5% EtOAc/95% hexane) R$_f$ 0.25; $^1$H NMR (CDCl$_3$) δ1.42 (s, 9H), 6.48 (br s, 1H), 7.01 (s, 1H), 7.10-7.18 (m, 2H), 7.26-7.30 (m, 1H), 7.36 (app t, J=7.72 Hz, 2H), 7.39 (br s, 1H), 7.50 (dm, J=6.99 Hz, 2H), 7.16 (dd, J=2.20, 7.72 Hz, 1H); $^{13}$C NMR (CDCl$_3$) δ 32.1 (3C), 34.8, 118.4, 118.8, 120.7, 121.1, 124.2, 127.7, 127.9, 128.2 (2C), 128.5, 129.0 (2C), 132.4, 132.5, 136.9, 153.1, 156.3; FAB-MS m/z (rel abundance) 419 ((M+H)$^+$, 6%), 421 ((M+H+2)$^+$, 4%).

D3. General Methods of Reduction of Nitro-Containing Aryl Ureas

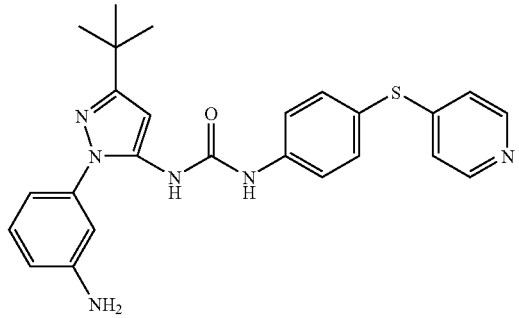

N-(1-(3-Aminophenyl)-3-tert-butyl-5-pyrazolyl)-N'-(4-(4-pyridinylthio)phenyl)urea: A solution of N-(1-(3-nitrophenyl)-3-tert-butyl-5-pyrazolyl)-N'-(4-(4-pyridinylthio)phenyl)urea (Prepared in methods analogous to those described in A1 and C1a; 0.310 g, 0.635 mmol) in acetic acid (20 mL) was placed under an atmosphere of Ar using a vacuum-degassed and argon-purge protocol. To this was added water (0.2 mL) followed by iron powder (325 mesh; 0.354 g, 6.35 mmol). The reaction mixture was stirred vigorously under argon at room temp. for 18 h, at which time TLC indicated the absence of starting material. The reaction mixture was filtered and the solids were washed copiously with water (300 mL). The orange solution was then brought to pH 4.5 by addition of NaOH pellets (a white precipitate forms). The resulting suspension was extracted with Et$_2$O (3×250 mL), and the combined organic layers were washed with a saturated NaHCO$_3$ solution (2×300 mL) until foaming ceased. The resulting solution was dried (MgSO$_4$) and concentrated under reduced pressure. The resulting white solid was purified by column chromatography (gradient from 30% acetone/70% CH$_2$Cl$_2$ to 50% acetone/50% CH$_2$Cl$_2$) to give the product as a white solid (0.165 g, 57%): TLC (50% acetone/50% CH$_2$Cl$_2$) R$_f$ 0.50; $^1$H NMR (DMSO-d$_6$) δ 1.24 (s, 9H), 5.40 (br s, 2H), 6.34 (s, 1H), 6.57 (d, J=8 Hz, 2H), 6.67 (s, 1H), 6.94 (d, J=6 Hz, 2H), 7.12 (app t, J=8 Hz, 1H), 7.47 (d, J=9 Hz, 2H), 7.57 (d, J=9 Hz, 2H), 8.31 (d, J=6 Hz, 2H), 8.43 (s, 1H), 9.39 (s, 1H); FAB-MS m/z 459 ((M+H)$^+$).

D4. General Methods of Acylation of Amine-Containing Aryl Ureas

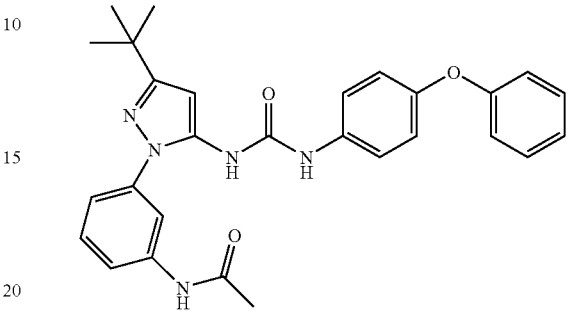

N-(1-(3-Acetamidophenyl)-3-tert-butyl-5-pyrazolyl)-N'-(4-phenoxyphenyl)urea: To a solution of N-(1-(3-aminophenyl)-3-tert-butyl-5-pyrazolyl)-N'-(4-phenoxyphenyl)urea (prepared using methods analogous to those described in A1, C1a and D3; 0.154 g, 0.349 mmol) in CH$_2$Cl$_2$ (10 mL) was added pyridine (0.05 mL) followed by acetyl chloride (0.030 mL, 0.417 mmol). The reaction mixture was stirred under argon at room temp. for 3 h, at which time TLC analysis indicated the absence of starting material. The reaction mixture was diluted with CH$_2$Cl$_2$ (20 mL), then the resulting solution was sequentially washed with water (30 mL) and a saturated NaCl solution (30 mL), dried (MgSO$_4$) and concentrated under reduced pressure. The resulting residue was purified by column chromatography (gradient from 5% EtOAc/95% hexane to 75% EtOAc/25% hexane) to give the product as a white solid (0.049 g, 30%): TLC (70% EtOAc/30% hexane) R$_f$ 0.32; $^1$H NMR (DMSO-d$_6$) δ 1.26 (s, 9H), 2.05 (s, 3H), 6.35 (s, 1H), 6.92-6.97 (m, 4H), 7.05-7.18 (m, 2H), 7.32-7.45 (m, 5H), 7.64-7.73 (m, 2H), 8.38 (s, 1H), 9.00 (s, 1H), 10.16 (s, 1H); FAB-MS m/z 484 ((M+H)$^+$).

The following compounds have been synthesized according to the General Methods listed above:

TABLE 1

2-Substituted-5-tert-butylpyrazolyl Ureas

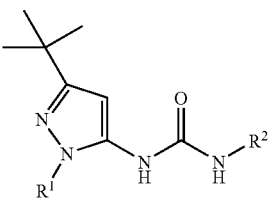

| Entry | R$^1$ | R$^2$ | mp (° C.) | TLC R$_f$ | Solvent System | Mass Spec. [Source] | Synth. Method |
|---|---|---|---|---|---|---|---|
| 1 | phenyl | 2,3-dichlorophenyl | | 0.42 | 20% EtOAc/ 80% hexane | 403 (M + H)+ [FAB] | A1, C1a |

TABLE 1-continued

2-Substituted-5-tert-butylpyrazolyl Ureas

| Entry | R¹ | R² | mp (° C.) | TLC R_f | Solvent System | Mass Spec. [Source] | Synth. Method |
|---|---|---|---|---|---|---|---|
| 2 | 4-NH₂-phenyl (methyl) | 2,3-dichlorophenyl (methyl) | | 0.50 | 67% EtOAc/ 33% hexane | 418 (M + H)+ [FAB] | A1, C1a, D3 |
| 3 | 2-Me-phenyl (methyl) | 2,3-dichlorophenyl (methyl) | | 0.27 | 20% EtOAc/ 80% hexane | 417 (M + H)+ [FAB] | A1, C1a |
| 4 | 2-pyridyl (methyl) | 2,3-dichlorophenyl (methyl) | | 0.47 | 20% EtOAc/ 80% hexane | 404 (M + H)+ [FAB] | A1, C1a |
| 5 | 4-CF₃-pyrimidin-2-yl (methyl) | 2,3-dichlorophenyl (methyl) | | 0.30 | 33% EtOAc/ 67% hexane | 473 (M + H)+ [FAB] | A1, C1a |
| 6 | 3-F-phenyl (methyl) | 2,3-dichlorophenyl (methyl) | | 0.27 | 100% EtOAc | 421 (M + H)+ [FAB] | A1, C1a |
| 7 | 4-Cl-phenyl (methyl) | 2,3-dichlorophenyl (methyl) | | 0.50 | 20% EtOAc/ 80% hexane | 437 (M + H)+ [FAB] | A1, C1a |
| 8 | 4-(SO₂Me)-phenyl (methyl) | 2,3-dichlorophenyl (methyl) | | 0.60 | 50% EtOAc/ 50% hexane | 481 (M + H)+ [FAB] | A1, C1a |
| 9 | 4-NO₂-phenyl (methyl) | 2,3-dichlorophenyl (methyl) | | 0.37 | 20% EtOAc/ 80% hexane | 448 (M + H)+ [FAB] | A1, C1a |
| 10 | 3-OMe-phenyl (methyl) | 2,3-dichlorophenyl (methyl) | | 0.35 | 20% EtOAc/ 80% hexane | 433 (M + H)+ [FAB] | A1, C1a |

TABLE 1-continued
2-Substituted-5-tert-butylpyrazolyl Ureas
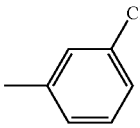
| Entry | R¹ | R² | mp (° C.) | TLC R_f | Solvent System | Mass Spec. [Source] | Synth. Method |
|---|---|---|---|---|---|---|---|
| 11 | 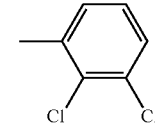 | 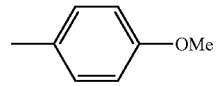 | | 0.40 | 20% EtOAc/ 80% hexane | 471 (M + H)+ [FAB] | A1, C1a |
| 12 | 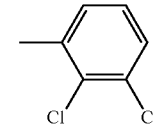 |  | | 0.22 | 20% EtOAc/ 80% hexane | 433 (M + H)+ [FAB] | A1, C1a |
| 13 | 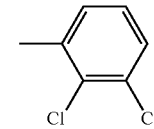 | 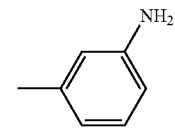 | | 0.51 | 20% EtOAc/ 80% hexane | 445 (M + H)+ [FAB] | A1, C1a |
| 14 | 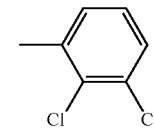 | 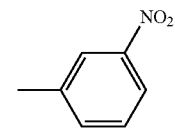 | | 0.39 | 50% EtOAc/ 50% hexane | 418 (M + H)+ [FAB] | A1, C1a, D3 |
| 15 | 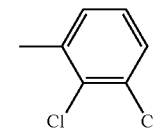 | 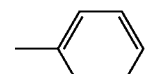 | | 0.31 | 30% EtOAc/ 70% hexane | 448 (M + H)+ [FAB] | A1, C1a |
| 16 | 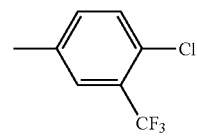 | 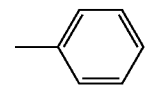 | 195-200 | | | 437 (M + H)+ [FAB] | A1, C1a |
| 17 | 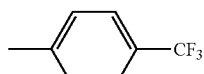 | 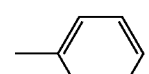 | 97-100 | | | 403 (M + H)+ [FAB] | A1, C1a |
| 18 | 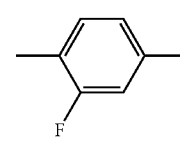 | 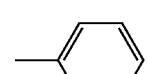 | 84-85 | | | 371 (M + H)+ [FAB] | A1, C1a |
| 19 | | 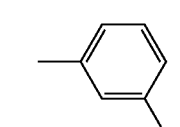 | 156-159 | | | 353 (M + H)+ [FAB] | A1, C1a |

TABLE 1-continued

2-Substituted-5-tert-butylpyrazolyl Ureas

| Entry | R¹ | R² | mp (° C.) | TLC R_f | Solvent System | Mass Spec. [Source] | Synth. Method |
|---|---|---|---|---|---|---|---|
| 20 | phenyl | 3-cyanophenyl | 168-169 | | | 360 (M + H)+ [FAB] | A1, C1a |
| 21 | phenyl | 4-nitrophenyl | 131-135 | | | 380 (M + H)+ [CI] | A1, C1a |
| 22 | 3-(acetylamino)phenyl | 4-phenoxyphenyl | | 0.31 | 70% EtOAc/ 30% hexane | 484 (M + H)+ [FAB] | A1, C1a, D3, D4 |
| 23 | 3-aminophenyl | 4-phenoxyphenyl | | 0.14 | 50% EtOAc/ 50% hexane | 442 (M + H)+ [FAB] | A1, C1a, D3 |
| 24 | 3-nitrophenyl | 4-phenoxyphenyl | | 0.19 | 30% EtOAc/ 70% hexane | 472 (M + H)+ [FAB] | A1, C1a |
| 25 | phenyl | 4-(pyridin-4-ylmethyl)phenyl | | 0.56 | 60% acetone/ 40% CH2Cl2 | 426 (M + H)+ [FAB] | A1, C2 |
| 26 | 4-pyridyl | 4-(pyridin-4-ylmethyl)phenyl | | 0.34 | 10% MeOH/ 90% CH2Cl2 | 427 (M + H)+ [FAB] | A1, C2 |
| 27 | 2,3-dichlorophenyl | 4-(pyridin-4-ylmethyl)phenyl | | 0.44 | 40% acetone/ 60% CH2Cl2 | 494 (M + H)+ [FAB] | A1, C2 |
| 28 | 4-fluorophenyl | 4-(pyridin-4-ylmethyl)phenyl | | 0.44 | 40% acetone/ 60% CH2Cl2 | 444 (M + H)+ [FAB] | A1, C2 |

TABLE 1-continued

2-Substituted-5-tert-butylpyrazolyl Ureas

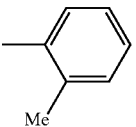

| Entry | R¹ | R² | mp (° C.) | TLC R$_f$ | Solvent System | Mass Spec. [Source] | Synth. Method |
|---|---|---|---|---|---|---|---|
| 29 | 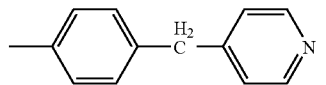 | 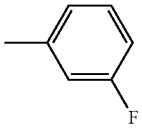 | | 0.46 | 40% acetone/ 60% CH2Cl2 | 440 (M + H)+ [FAB] | A1, C2 |
| 30 | 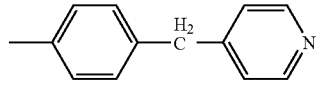 | 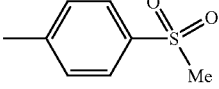 | | 0.48 | 40% acetone/ 60% CH2Cl2 | 444 (M + H)+ [FAB] | A1, C2 |
| 31 | 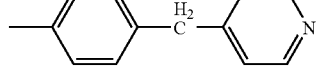 | 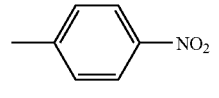 | | 0.34 | 40% acetone/ 60% CH2Cl2 | 504 (M + H)+ | A1, C2 |
| 32 | 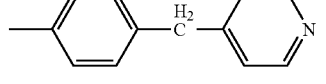 | 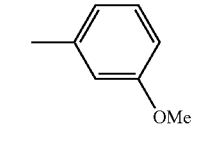 | | 0.47 | 40% acetone/ 60% CH2Cl2 | 471 (M + H)+ [FAB] | A1, C2 |
| 33 | 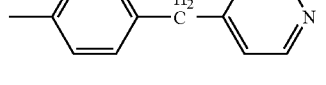 | 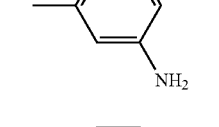 | | 0.51 | 60% acetone/ 40% CH2Cl2 | 456 (M + H)+ [FAB] | A1, C2 |
| 34 | 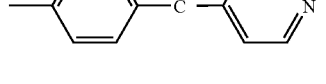 | 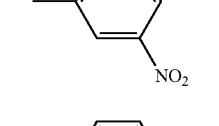 | | 0.50 | 50% acetone/ 50% CH2Cl2 | 441 (M + H)+ [FAB] | A1, C2, D3 |
| 35 | 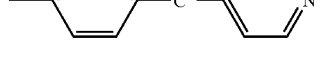 | 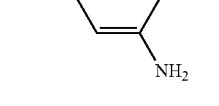 | | 0.43 | 30% acetone/ 70% CH2Cl2 | 471 (M + H)+ [FAB] | A1, C2 |
| 36 | 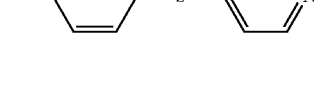 | 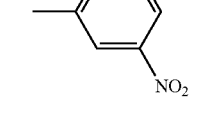 | | 0.50 | 50% acetone/ 50% CH2Cl2 | 459 (M + H)+ [FAB] | A1, C2, D3 |
| 37 | 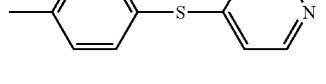 | | | 0.47 | 30% acetone/ 70% CH2Cl2 | 489 (M + H)+ [FAB] | A1, C2 |

TABLE 1-continued
2-Substituted-5-tert-butylpyrazolyl Ureas
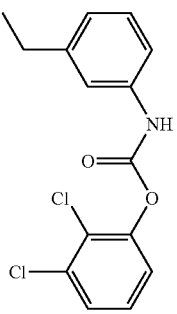
| Entry | R¹ | R² | mp (° C.) | TLC R$_f$ | Solvent System | Mass Spec. [Source] | Synth. Method |
|---|---|---|---|---|---|---|---|
| 38 | 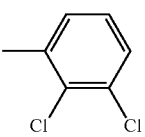 | 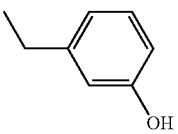 | | 0.47 | 50% EtOAc/ 50% hexane | 620 (M + H)+ [FAB] | A1, C2 |
| 39 | 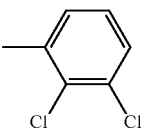 | 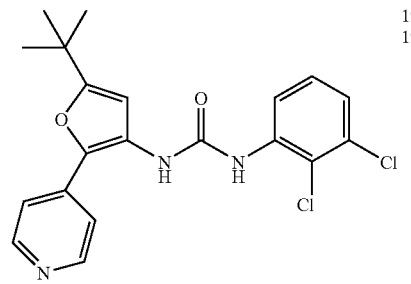 | | 0.34 | 50% EtOAc/ 50% hexane | 433 (M + H)+ [FAB] | A1, C2 |
TABLE 2
Additional Ureas
| Entry | R² | mp (° C.) | TLC R$_f$ | Solvent System | Mass Spec. | Synth. Method |
|---|---|---|---|---|---|---|
| 40 | 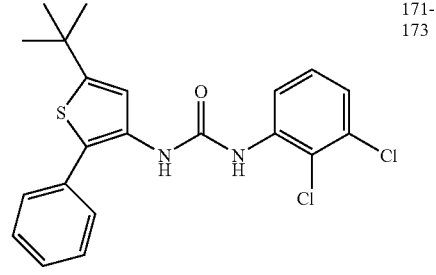 | 195- 198 | 0.47 | 60% EtOAc/ 40% hexane | 404 (M + H)+ [FAB] | A2, C1b |
| 41 |  | 171- 173 | 0.25 | 5% EtOAc/ 95% hexane | 419 (M + H)+ [FAB] | A3, C1c, D1, D2 |

BIOLOGICAL EXAMPLES

In Vitro raf Kinase Assay:

In an in vitro kinase assay, raf is incubated with MEK in 20 mM Tris-HCl, pH 8.2 containing 2 mM 2-mercaptoethanol and 100 mM NaCl. This protein solution (20 µL) is mixed with water (5 µL) or with compounds diluted with distilled water from 10 mM stock solutions of compounds dissolved in DMSO. The kinase reaction is initiated by adding 25 µL [γ-$^{33}$P]ATP (1000-3000 dpm/pmol) in 80 mM Tris-HCl, pH 7.5, 120 mM NaCl, 1.6 mM DTT, 16 mM $MgCl_2$. The reaction mixtures are incubated at 32° C., usually for 22 min. Incorporation of $^{33}$P into protein is assayed by harvesting the reaction onto phosphocellulose mats, washing away free counts with a 1% phosphoric acid solution and quantitating phosphorylation by liquid scintillation counting. For high throughput screening, 10 µM ATP and 0.4 µM MEK are used. In some experiments, the kinase reaction is stopped by adding an equal amount of Laemmli sample buffer. Samples are boiled 3 min and the proteins resolved by electrophoresis on 7.5% Laemmli gels. Gels are fixed, dried and exposed to an imaging plate (Fuji). Phosphorylation is analyzed using a Fujix Bio-Imaging Analyzer System.

All compounds exemplified displayed $IC_{50}$s of between 10 nM and 10 µM.

Cellular Assay:

For in vitro growth assay, human tumor cell lines, including but not limited to HCT116 and DLD-1, containing mutated K-ras genes are used in standard proliferation assays for anchorage dependent growth on plastic or anchorage independent growth in soft agar. Human tumor cell lines were obtained from ATCC (Rockville Md.) and maintained in RPMI with 10% heat inactivated fetal bovine serum and 200 mM glutamine. Cell culture media and additives are obtained from Gibco/BRL (Gaithersburg, Md.) except for fetal bovine serum (JRH Biosciences, Lenexa, Kans.). In a standard proliferation assay for anchorage dependent growth, 3×10$^3$ cells are seeded into 96-well tissue culture plates and allowed to attach overnight at 37° C. in a 5% $CO_2$ incubator. Compounds are titrated in media in dilution series and added to 96 well cell cultures. Cells are allowed to grow 5 days typically with a feeding of fresh compound containing media on day three. Proliferation is monitored by measuring metabolic activity with standard XTT colorimetric assay (Boehringer Mannheim) measured by standard ELISA plate reader at OD 490/560, or by measuring $^3$H-thymidine incorporation into DNA following an 8 h culture with 1 µCu $^3$H-thymidine, harvesting the cells onto glass fiber mats using a cell harvester and measuring $^3$H-thymidine incorporation by liquid scintillant counting.

For anchorage independent cell growth, cells are plated at 1×10$^3$ to 3×10$^3$ in 0.4% Seaplaque agarose in RPMI complete media, overlaying a bottom layer containing only 0.64% agar in RPMI complete media in 24-well tissue culture plates. Complete media plus dilution series of compounds are added to wells and incubated at 37° C. in a 5% $CO_2$ incubator for 10-14 days with repeated feedings of fresh media containing compound at 3-4 day intervals. Colony formation is monitored and total cell mass, average colony size and number of colonies are quantitated using image capture technology and image analysis software (Image Pro Plus, media Cybernetics).

These assays establish that the compounds of formula I are active to inhibit raf kinase activity and to inhibit oncogenic cell growth.

In Vivo Assay:

An in vivo assay of the inhibitory effect of the compounds on tumors (e.g., solid cancers) mediated by raf kinase can be performed as follows:

CDI nu/nu mice (6-8 weeks old) are injected subcutaneously into the flank at 1×10$^6$ cells with human colon adenocarcinoma cell line. The mice are dosed i.p., i.v. or p.o. at 10, 30, 100, or 300 mg/Kg beginning on approximately day 10, when tumor size is between 50-100 mg. Animals are dosed for 14 consecutive days once a day; tumor size was monitored with calipers twice a week.

The inhibitory effect of the compounds on raf kinase and therefore on tumors (e.g., solid cancers) mediated by raf kinase can further be demonstrated in vivo according to the technique of Monia et al. (*Nat. Med.* 1996, 2, 668-75).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula I or a pharmaceutically acceptable salt thereof

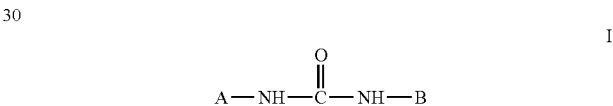

wherein A is

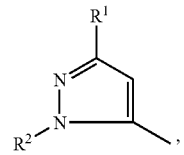

wherein $R^1$ is $C_3$-$C_{10}$ alkyl, $C_3$-$C_{10}$ cycloalkyl, up to per-halosubstituted $C_1$-$C_{10}$ alkyl or up to per-halosubstituted $C_3$-$C_{10}$ cycloalkyl;

B is phenyl, pyridinyl, or naphthyl, substituted by —M—L$^1$; and is optionally substituted by one or more substituents independently selected from the group consisting of halogen, up to per-halosubstitution, and $X_n$, wherein n is 0-2 and each X is independently selected from the group consisting of —CN, —$CO_2R^5$, —C(O)NR$^5$R$^{5'}$, —C(O)R$^5$, —$NO_2$, —OR$^5$, —SR$^5$, —NR$^5$R$^{5'}$, —NR$^5$C(O)OR$^{5'}$, —NR$^5$C(O)R$^{5'}$, $C_1$-$C_{10}$ alkyl, $C_2$-$C_{10}$ alkenyl, $C_1$-$C_{10}$ alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_2$-$C_{10}$alkenyl, substituted $C_1$-$C_{10}$ alkoxyl, substituted $C_3$-$C_{10}$ cycloalkyl, up to per-halosubstituted $C_6$-$C_{14}$ aryl, up to per-halosubstituted $C_3$-$C_{13}$ heteroaryl and substituted $C_4$-$C_{23}$ alkheteroaryl and —M—L$^1$;

where X is a substituted group, it is substituted by one or more substituents independently selected from the group consisting of —CN, —$CO_2R^5$, —C(O)R$^5$, —C(O)NR₅R⁵', —OR⁵, —SR⁵, —NR⁵R⁵', —NO₂, —NR⁵C(O)R⁵', —NR⁵C(O)OR⁵' and halogen up to per-halosubstitution;

wherein R⁵ and R⁵' are independently selected from H, $C_1$-$C_{10}$ alkyl, $C_2$-$C_{10}$ alkenyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_2$-$C_{10}$ alkenyl, up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl, wherein M is —O—, —S—, or —(CH₂)—$_m$ m=1-3, and $X^a$ is halogen; and L¹ is pyridinyl, quinolinyl or isoquinolinyl, optionally substituted by halogen up to per-halosubstitution and optionally substituted by $Z_{n1}$, wherein n1 is 0 to 3 and each Z is independently —CN, —CO₂R⁵, —C(O)NR⁵R⁵', —C(O)NR⁵, —NO₂, —OR⁵, —SR⁵, —NR⁵R⁵', —NR⁵C(O)OR⁵', —C(O)R⁵, NR⁵C(O)R⁵', $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, substituted $C_1$-$C_{10}$ alkyl, substituted $C_3$-$C_{10}$ cycloalkyl, substituted $C_7$-$C_{24}$ alkaryl or substituted $C_4$-$C_{23}$ alkheteroaryl;

wherein if Z is a substituted group, it is substituted by the one or more substituents independently selected from the group consisting of —CN, —CO₂R⁵, —C(O)NR⁵R⁵', —OR⁵, —SR⁵, —NO₂, —NR⁵R⁵', —NR⁵C(O)R⁵' and —NR⁵C(O)OR⁵', and wherein R² is unsubstituted phenyl, unsubstituted pyridinyl, substituted phenyl or substituted pyridinyl wherein if R² is a substituted group, it is substituted by one or more substituents independently selected from the group consisting of halogen, up to per-halosubstitution, and $V_n$, wherein n=0-3 and each V is independently selected from the group consisting of —CN, —CO₂R⁵, —C(O)NR⁵R⁵', —OR⁵, —SR⁵, —NR⁵R⁵', —C(O)R⁵, —OC(O)NR⁵R⁵', —NR⁵C(O)OR⁵', —SO₂R⁵, —SOR⁵, —NR⁵C(O)R⁵', —NO₂, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{24}$ alkheteroaryl, substituted $C_1$-$C_{10}$ alkyl, substituted $C_3$-$C_{10}$ cycloalkyl, substituted $C_6$-$C_{14}$ aryl, substituted $C_3$-$C_{13}$ heteroaryl, substituted $C_7$-$C_{24}$ alkaryl and substituted $C_4$-$C_{24}$ alkheteroaryl, where if V is a substituted group, it is substituted by one or more substituents independently selected from the group consisting of halogen, up to per-halosubstitution, —CN, —CO₂R⁵, —C(O)R⁵, —C(O)NR⁵R⁵, —NR⁵R⁵', —OR⁵, —SR⁵, —NR⁵C(O)R⁵', —NR⁵C(O)OR⁵' and —NO₂;

wherein R⁵ and R⁵' are each independently as defined above.

2. A compound of claim 1, wherein R1 is t-butyl and R2 is unsubstituted or substituted phenyl.

3. A compound of claim 1 of the formula

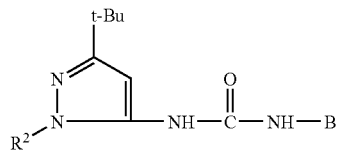

wherein B and R² are as defined in claim 1.

4. A compound of claim 1 wherein one of the following combinations is satisfied:

R²=unsubstituted phenyl, B=phenyl and L¹ is pyridinyl, quinolinyl or isoquinolinyl, R²=unsubstituted phenyl, B=pyridinyl and L¹ is pyridinyl, quinolinyl or isoquinolinyl, R²=unsubstituted phenyl, B=naphthyl and L¹ is pyridinyl, quinolinyl or isoquinolinyl, R²=unsubstituted pyridinyl, B=phenyl and L¹ is pyridinyl, quinolinyl or isoquinolinyl, R²=unsubstituted pyridinyl, B=pyridinyl and L¹ is pyridinyl, quinolinyl or isoquinolinyl, R²=unsubstituted pyridinyl, B=naphthyl and L¹ is pyridinyl, quinolinyl or isoquinolinyl, R²=substituted phenyl, B=phenyl and L¹ is pyridinyl, quinolinyl or isoquinolinyl, R²=substituted phenyl, B=pyridinyl and L¹ is pyridinyl, quinolinyl or isoquinolinyl, R²=substituted phenyl, B=naphthyl and L¹ is pyridinyl, quinolinyl or isoquinolinyl, R²=substituted pyridinyl, B=phenyl and L¹ is pyridinyl, quinolinyl or isoquinolinyl, R²=substituted pyridinyl, B=pyridinyl and L¹ is pyridinyl, quinolinyl or isoquinolinyl, or R²=substituted pyridinyl, B=naphthyl and L¹ is pyridinyl, quinolinyl isoquinolinyl.

5. A compound of Formula I or a pharmaceutically acceptable salt thereof

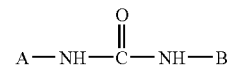

wherein A is

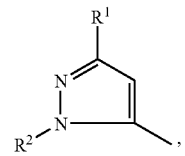

wherein R¹ is $C_3$-$C_{10}$ alkyl, $C_3$-$C_{10}$ cycloalkyl, up to per-halosubstituted $C_1$-$C_{10}$ alkyl or up to per-halosubstituted $C_3$-$C_{10}$ cycloalkyl;

wherein n is 0-2 and each X is independently selected from the group consisting of —CN, —CO₂R⁵, —C(O)NR⁵R⁵', —C(O)R⁵, —NO₂, —OR⁵, —SR⁵, —NR⁵R⁵', NR⁵C(O)OR⁵', —NR⁵C(O)R⁵', $C_1$-$C_{10}$ alkyl, $C_2$-$C_{10}$ alkenyl, $C_1$-$C_{10}$ alkoxy, $C_3$-$C_{10}$ cycloalkyl, $C_6$-$C_{14}$ aryl, $C_7$-$C_{24}$ alkaryl, $C_3$-$C_{13}$ heteroaryl, $C_4$-$C_{23}$ alkheteroaryl, substituted $C_1$-$C_{10}$ alkyl, substituted $C_2$-$C_{10}$ alkenyl, substituted $C_1$-$C_{10}$ alkoxyl, substituted $C_3$-$C_{10}$ cycloalkyl, up to per-halosubstituted $C_6$-$C_{14}$ aryl, up to per-halosubstituted $C_3$-$C_{13}$ heteroaryl and substituted $C_4$-$C_{23}$ alkheteroaryl and —M—L¹;

where X is a substituted group, it is substituted by one or more substituents independently selected from the group consisting of —CN, —CO₂R⁵, —C(O)R⁵, —C(O)NR⁵R⁵', —OR⁵, —SR⁵, —NR⁵R⁵', —NO₂, —NR⁵C(O)R⁵', —NR⁵C(O)OR⁵' and halogen up to per-halosubstitution;

wherein R⁵ and R⁵' are independently selected from H, $C_1$-$C_{10}$ alkyl, $C_2$-$C_{10}$ alkenyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, up to per-halosubstituted $C_1$-$C_{10}$ alkyl, up to per-halosubstituted $C_2$-$C_{10}$ alkenyl, up to per-halosubstituted $C_3$-$C_{10}$ cycloalkyl, up to per-halosubstituted $C_6$-$C_{14}$ aryl and up to per-halosubstituted $C_3$-$C_{13}$ heteroaryl, wherein M is —O—, —S—, —N($R^5$)—, —($CH_2$)$_m$—, —C(O)—, —CH(OH)—, —($CH_2$)$_m$O—, —$NR^5$C(O)—, —C(O)$NR^5$, —O($CH_2$)$_m$—, —($CH_2$)$_m$S—, —($CH_2$)$_m$N($R^5$)—, —CH$X^a$—, —C$X^a{}_2$—, —S—($CH_2$)$_m$— or —N($R^5$)($CH_2$)$_m$—, m=1-3, and $X^a$ is halogen; and $L^1$ is pyridinyl, pyrimidinyl, pyrazinyl, pyridazinyl, quinolinyl, isoquinolinyl, phthalimidinyl, furyl, thienyl, pyrrolyl, imidazolyl, pyrazolyl, oxazolyl, isoxazolyl, thiazolyl, isothiazolyl, benzofuryl, benzothienyl, indolyl, benzopyrazolyl, benzoxazolyl, benzisoxazolyl, benzothiazolyl or benzisothiazolyl, optionally substituted by halogen up to per-halosubstitution and optionally substituted by $Z_{n1}$, wherein n1 is 0 to 3 and each Z is independently —CN, —$CO_2R^5$, —C(O)$NR^5R^{5'}$, —C(O)$NR^5$, —$NO_2$, —$OR^5$, —$SR^5$, —$NR^5R^{5'}$, —$NR^5$C(O)$OR^{5'}$, —C(O)$R^5$, $NR^5$C(O)$R^{5'}$, $C_1$-$C_{10}$ alkyl, $C_3$-$C_{10}$ cycloalkyl, $C_6$-$C_{14}$ aryl, $C_3$-$C_{13}$ heteroaryl, $C_7$-$C_{24}$ alkaryl, $C_4$-$C_{23}$ alkheteroaryl, substituted $C_1$-$C_{10}$ alkyl, substituted $C_3$-$C_{10}$ cycloalkyl, substituted $C_7$-$C_{24}$ alkaryl or substituted $C_4$-$C_{23}$ alkheteroaryl;

wherein if Z is a substituted group, it is substituted by the one or more substituents independently selected from the group consisting of —CN, —$CO_2R^5$, —C(O)$NR^5R^{5'}$, —$OR^5$, —$SR^5$, —$NO_2$, —$NR^5R^{5'}$, —$NR^5$C(O)$R^{5'}$ and —$NR^5$C(O)$OR^{5'}$.

6. A compound as in claim 5 wherein B is optionally substituted pyridinyloxyphenyl, benzothiazolyloxyphenyl, benzothiazolylthiophenyl, pyrimidinyloxyphenyl, quinolinylthiophenyl, and phthalimidylmethylphenyl and $R^2$ is phenyl, substituted phenyl, pyridinyl or substituted pyridinyl.

7. A pharmaceutical composition comprising an effective amount of a compound of claim 1 and a pharmaceutically acceptable carrier.

* * * * *

UNITED STATES PATENT AND TRADEMARK OFFICE
CERTIFICATE OF CORRECTION

PATENT NO. : 7,329,670 B1
APPLICATION NO. : 09/472232
DATED : February 12, 2008
INVENTOR(S) : Jacques Dumas It is certified that error appears in the above-identified patent and that said Letters Patent is hereby corrected as shown below:

Column 37, line 1, reads "—C(O)NR$_5$R$^{5'}$" should read -- —C(O)NR$^5$R$^{5'}$ --
Column 37, line 12, reads "-(CH$_2$)-$_m$" should read -- -(CH$_2$)-$_m$,--
Column 37, line 31, reads "substituted pyridinyl" should read --substituted pyridinyl,--
Column 37, line 55, reads "R1 is t-butyl and R2" should read --R$^1$ is t-butyl and R$^2$--
Column 38, line 26, reads "quinolinyl isoquinolinyl." should read --quinolinyl or isoquinolinyl.--

Signed and Sealed this

Seventeenth Day of March, 2009

JOHN DOLL
*Acting Director of the United States Patent and Trademark Office*